US010512788B2

(12) United States Patent
Johnson et al.

(10) Patent No.: US 10,512,788 B2
(45) Date of Patent: Dec. 24, 2019

(54) VASCULAR ACCESS DEVICE WITH INTEGRATED LIGHT GUIDE

(71) Applicant: UVLrx Therapeutics, Inc., Santa Barbara, CA (US)

(72) Inventors: Scot Johnson, Lutz, FL (US); Michael Harter, Tampa, FL (US); Victor Josef Scheeren, Port Richey, FL (US)

(73) Assignee: UVLrx Therapeutics, Inc., Oldsmar, FL (US)

( * ) Notice: Subject to any disclaimer, the term of this patent is extended or adjusted under 35 U.S.C. 154(b) by 0 days.

(21) Appl. No.: 15/814,873

(22) Filed: Nov. 16, 2017

(65) Prior Publication Data

US 2018/0078781 A1 Mar. 22, 2018

Related U.S. Application Data

(62) Division of application No. 14/323,217, filed on Jul. 3, 2014, now Pat. No. 9,827,438.

(60) Provisional application No. 61/887,670, filed on Oct. 7, 2013, provisional application No. 61/887,845, filed on Oct. 7, 2013, provisional application No. 61/887,800, filed on Oct. 7, 2013, provisional application No. 61/957,513, filed on Jul. 5, 2013, provisional application No. 61/957,465, filed on Jul. 3, 2013, provisional application No. 61/957,463, filed on Jul. 5, 2013, provisional application No. 61/957,464, filed on Jul. 3, 2013.

(51) Int. Cl.
*A61N 5/06* (2006.01)
*G02B 6/38* (2006.01)

(52) U.S. Cl.
CPC ......... *A61N 5/0601* (2013.01); *G02B 6/3825* (2013.01); *G02B 6/3851* (2013.01); *A61N 2005/0602* (2013.01); *A61N 2005/063* (2013.01); *A61N 2005/0661* (2013.01); *G02B 6/3816* (2013.01)

(58) Field of Classification Search
CPC .. A61N 5/0601; A61N 5/0603; A61N 5/0613; A61N 2005/0602; A61N 2005/063; A61N 2005/0632; A61N 2005/0642; A61N 2005/0643
USPC ......... 607/88–90, 92, 93, 96, 100, 104–106; 606/7, 13–16, 19–22, 27, 28; 604/19–21, 604/27, 39–45; 600/101, 104, 105, 114, 600/130
See application file for complete search history.

(56) References Cited

U.S. PATENT DOCUMENTS 4,519,390 A 5/1985 Home
4,718,417 A 1/1988 Kittrell et al.
(Continued)

*Primary Examiner* — Ahmed M Farah
(74) *Attorney, Agent, or Firm* — The Emanuelson Firm; Kenneth T. Emanuelson

(57) ABSTRACT

A system for irradiation of a vascular space and its contents is presented. An adapter device having a vascular access end and an optical interface end can include a waveguide affixed within a waveguide lumen and extending outwardly through the vascular access end. The optical interface end includes a tapered terminus configured to engage with a cavity of an optical connector adapter, creating an optical interface between the waveguide of the adapter device and a waveguide of a light or radiation source. The adapter device enables the simultaneous administration of radiation and exogenous fluids to a patient while maintaining the optical interface isolated from any fluids.

6 Claims, 31 Drawing Sheets

(56) References Cited

U.S. PATENT DOCUMENTS

| | | | |
|---|---|---|---|
| 5,093,877 A * | 3/1992 | Aita | A61B 18/245 |
| | | | 385/33 |
| 5,169,395 A * | 12/1992 | Narciso, Jr. | A61N 5/0601 |
| | | | 606/14 |
| 5,452,391 A | 9/1995 | Chou et al. | |
| 5,833,682 A | 11/1998 | Amplatz et al. | |
| 5,957,917 A * | 9/1999 | Doiron | A61N 5/0601 |
| | | | 606/15 |
| 5,964,751 A | 10/1999 | Amplatz et al. | |
| 6,117,128 A | 9/2000 | Gregory | |
| 6,231,568 B1 * | 5/2001 | Loeb | A61B 18/24 |
| | | | 606/15 |
| 6,695,772 B1 | 2/2004 | Bon et al. | |
| 8,265,446 B2 * | 9/2012 | Lonero | A61B 18/22 |
| | | | 385/134 |
| 8,413,664 B2 * | 4/2013 | Appling | A61B 18/24 |
| | | | 128/898 |
| 8,961,398 B2 | 2/2015 | Makower et al. | |
| 9,814,899 B2 * | 11/2017 | Johnson | A61N 5/0601 |
| 2003/0114842 A1 * | 6/2003 | DiStefano | A61B 18/24 |
| | | | 606/7 |
| 2004/0010248 A1 | 1/2004 | Appling et al. | |
| 2004/0116912 A1 | 6/2004 | Appling | |
| 2005/0245892 A1 * | 11/2005 | Elkins | A61M 25/0043 |
| | | | 604/508 |
| 2005/0245982 A1 | 11/2005 | Elkins et al. | |
| 2008/0249517 A1 | 10/2008 | Svanberg | |
| 2008/0275483 A1 * | 11/2008 | Makower | A61B 17/24 |
| | | | 606/192 |
| 2009/0192505 A1 | 7/2009 | Askew et al. | |
| 2010/0292533 A1 | 11/2010 | Kasahara et al. | |
| 2013/0116679 A1 | 5/2013 | Van der Weide et al. | |
| 2015/0018753 A1 | 1/2015 | Johnson et al. | |

* cited by examiner

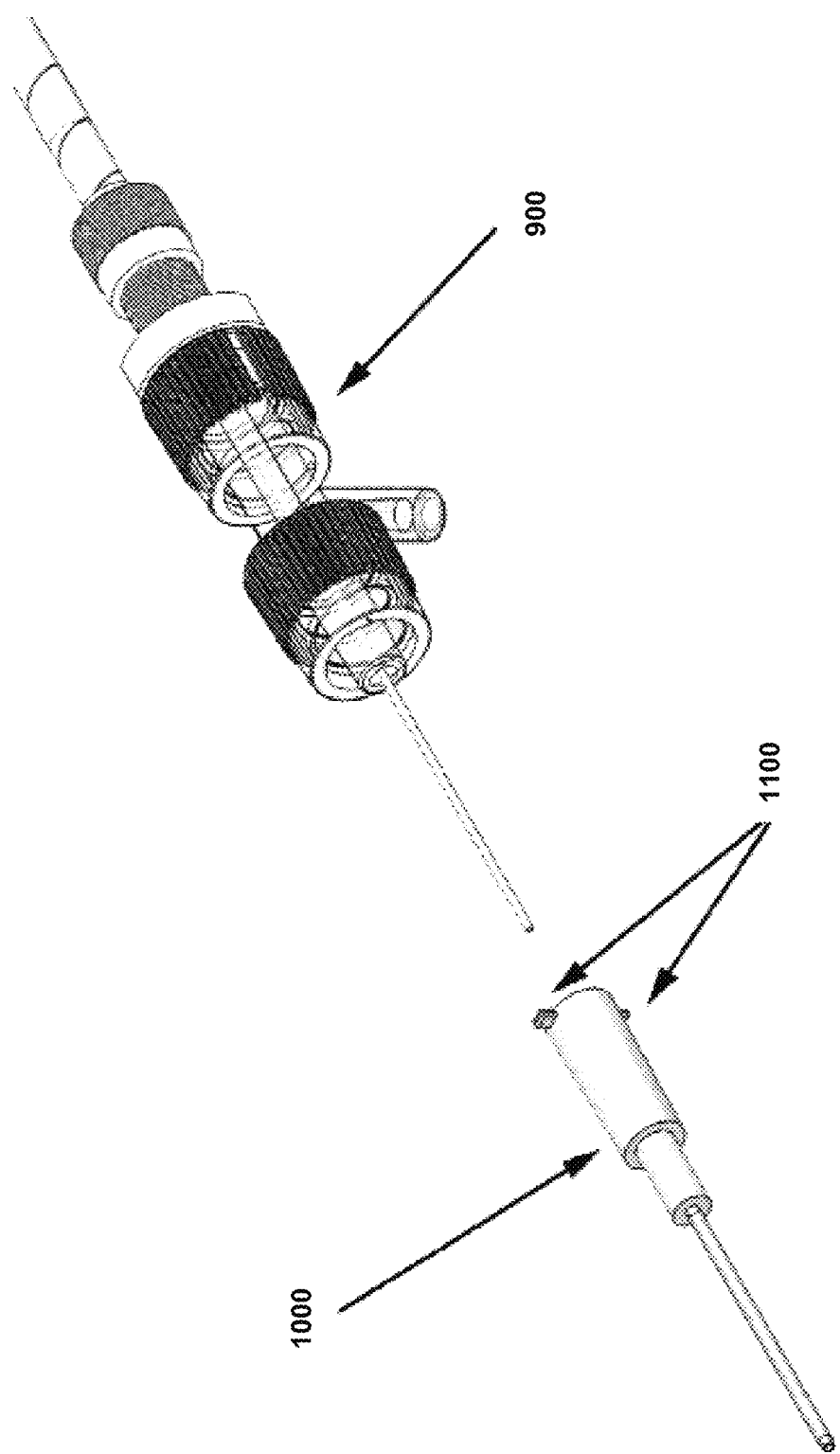

| 18 gauge catheter | | | | 20 gauge catheter | | | | 22 gauge catheter | | |
| --- | --- | --- | --- | --- | --- | --- | --- | --- | --- | --- |
| | in | mm | | | in | mm | | | in | mm |
| Catheter ID | 0.0360 | 0.9144 | | Catheter ID | 0.0280 | 0.7112 | | Catheter ID | 0.0220 | 0.5588 |
| Catheter ID area | 0.0010 | 0.0259 | | Catheter ID area | 0.0006 | 0.0156 | | Catheter ID area | 0.0004 | 0.0097 |
| ID of a 24 gauge catheter (desired flow rate) | 0.0120 | 0.3048 | | ID of a 24ga catheter (desired flow rate) | 0.0120 | 0.3048 | | ID of a 24ga catheter (desired flow rate) | 0.0120 | 0.3048 |
| Sectional area of a 24 gauge catheter | 0.0001 | 0.0029 | | Sectional area of a 24 gauge catheter | 0.0001 | 0.0029 | | Sectional area of a 24 gauge catheter | 0.0001 | 0.0029 |
| Residual sectional area remaining | 0.0009 | 0.0230 | | Residual sectional area remaining | 0.0005 | 0.0128 | | Residual sectional area remaining | 0.0003 | 0.0068 |
| Calculated maximum allowable sheath radius | 0.0170 | 0.4311 | | Calculated maximum allowable sheath radius | 0.0126 | 0.3213 | | Calculated maximum allowable sheath radius | 0.0092 | 0.2342 |
| Calculated maximum allowable sheath diameter | 0.0339 | 0.8621 | | Calculated maximum allowable sheath diameter | 0.0253 | 0.6426 | | Calculated maximum allowable sheath diameter | 0.0184 | 0.4684 |
| 21 gauge XTW type tube: OD | 0.0320 | 0.8128 | | 23 gauge XTW type tube: OD | 0.0250 | 0.6350 | | 26 gauge XTW type tube: OD | 0.0280 | 0.7112 |
| 21 gauge XTW type tube: ID | 0.0250 | 0.6350 | | 23 gauge XTW type tube: ID | 0.0190 | 0.4826 | | 26 gauge XTW type tube: ID | 0.0140 | 0.3556 |
| Optical fiber with effective OD of 600μm | 0.0236 | 0.6000 | | Optical fiber with effective OD of 480μm | 0.0189 | 0.4800 | | Optical fiber with effective OD of 330μm | 0.0130 | 0.3300 |
| | | | | | | | | Optical fiber with effective OD of 240μm | 0.0094 | 0.2400 |
| Gap diameter | 0.0014 | 0.0350 | | Gap diameter | 0.0001 | 0.0026 | | Gap diameter (330μm) | 0.0010 | 0.0256 |
| Gap spacing | 0.0007 | 0.0175 | | Gap spacing | 0.0001 | 0.0013 | | Gap space (330 μm) | 0.0005 | 0.0128 |
| | | | | | | | | Gap diameter (240μm) | 0.0046 | 0.1156 |
| | | | | | | | | Gap space (240μm) | 0.0023 | 0.0578 |

Figure 11

VASCULAR ACCESS DEVICE WITH INTEGRATED LIGHT GUIDE

This application is a divisional application of U.S. patent application Ser. No. 14/323,217, filed Jul. 3, 2014, which claims priority to U.S. Provisional Application No. 61/887,670 filed Oct. 7, 2013, U.S. Provisional Application No. 61/957,464, filed Jul. 3, 2013, U.S. Provisional Application No. 61/957,465, filed Jul. 3, 2013, U.S. Provisional Application No. 61/957,463 (filed Jul. 3, 2013), U.S. Provisional Application No. 61/957,513 (filed Jul. 5, 2013), 61/887,845 (filed Oct. 7, 2013), and 61/887,800 (filed Oct. 7, 2013), U.S. Provisional Application No. 61/887,670, U.S. Provisional Application No. 61/957,464, U.S. Provisional Application No. 61/957,465, U.S. Provisional Application No. 61/957,463, U.S. Provisional Application No. 61/957,513, U.S. Provisional Application No. 61/887,845 and U.S. Provisional Application No. 61/887,800, as well as all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The present invention generally relates to systems, devices and methods for treatment of human blood. More particularly, the present invention relates to systems, devices and methods for irradiating human blood in vivo.

BACKGROUND

It has long been accepted that certain wavelengths of electromagnetic radiation, such as ultraviolet light, have the ability to affect biological and chemical structures. For example, the formation of thymine dimers under the influence of ultraviolet light is well known and has been utilized to sterilize surfaces by killing or inactivating a variety of pathogens. In the early 1900's efforts were made to incorporate exposure to ultraviolet light as a treatment modality for various diseases, including bacterial and viral infections. Procedures were typically extracorporeal; a volume of blood would be removed from a patient, irradiated to modify a patient's immune response and/or inactivate pathogens, and returned to the patient. Such efforts were hindered, however, by the sources of ultraviolet light available at the time. UV lamps of the time period did not operate reliably, produced inconsistent illumination, and generated large amounts of heat. The development of effective and reliable antibiotics that were easily administered resulted in a loss of interest in this therapeutic approach.

The increasing prevalence of antibiotic-resistant pathogens and the recognition of potential effectiveness for the treatment of noninfectious medical conditions have led to an increasing interest in the use of blood irradiation as a treatment modality. A variety of devices for improved extracorporeal irradiation of blood have been proposed.

For example, United States Patent Application No. 2004/0116912 to Appling and United States Patent Application No. 2004/0010248 to Appling, et al, both discuss endovascular laser treatment devices used with an optical fiber running from a laser source to the patient's body. However, the length of the singular fibers in these approaches present installation challenges to the administering personnel. Additionally, if the optical fiber has to be replaced at any time after introduction into the patient, the entire fiber must be withdrawn from the patient's body and a new one installed.

Other approaches have included devices whereby the fiber is divided. For example, United States Patent Application No. 2008/0249517 to Svanberg discusses connecting a light guide within an adapter body to a light guide of a light source via an optical connector using a threaded connection. However, the coupling and uncoupling of adapter body and optical connector require the rotation of the adapter body and/or optical connector, which risks injury to the patient if the coupling or uncoupling occurs while the adapter body is connected to an inserted catheter or needle.

This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

While certain devices and methods are known in the art to irradiate blood, all or almost all of them suffer from one or more disadvantages. Thus, there is still a need for simple system for the effective in vivo irradiation of blood.

SUMMARY OF THE INVENTION

The inventive subject matter discloses systems and devices that provide a waveguide, safe and convenient vascular and/or lymphatic access for the waveguide, and an effective and efficient optical coupling between the waveguide and one or more sources of electromagnetic radiation. When the system is in place at least a portion of the waveguide is in optical communication with the vasculature and/or lymphatic system of an individual undergoing treatment. Electromagnetic radiation, for example ultraviolet and/or visible light, can be transferred from the light source to the waveguide, and from the waveguide to the vasculature and/or lymphatic system of the individual undergoing treatment, thereby providing in vivo irradiation of blood and/or other body fluids.

The system can include an adapter device and an optical interface that can be coupled together to align a waveguide within the adapter with a waveguide (e.g., a light delivery cable) of a light source such that the radiation from the source can be administered to a patient's body in vivo. The adapter device can include a fluid port that permits exogenous fluids to be administered during this irradiation. The optical interface between the waveguide and the light delivery cable can be isolated from body fluids, exogenous fluids, and/or both body fluids and exogenous fluids. In embodiments of the inventive concept the optical interface does not include active optics, and most preferably a dry optic coupling between a light delivery cable and the waveguide (i.e., light does not travel through any liquid at the interface between the light delivery cable and the waveguide).

In embodiments, the adapter device can be coupled to the optical interface via a tapered end of the adapter device and a corresponding cavity in the optical interface, such that the waveguide of the adapter device and the waveguide of the radiation source are brought into alignment within required angular and distance tolerances. The adapter device can further include protrusions such as tabs or threads that engage with a slip lock ring on the optical interface.

In embodiments of the inventive concept the optical interface can be configured to accept industry standard optical coupling, for example a SMA-905 optical fiber connector. In other embodiments of the inventive concept an optical adapter may be interposed between a waveguide of the adapter device and an optical fiber connector that is in optical communication with a source of electromagnetic radiation.

In some embodiments of the inventive concept the adapter device can include machine readable indicia (for example, a one dimensional barcode, a two dimensional barcode, an RFID device, and/or an optical RFID or OPID device). Such machine readable indicia can be utilized to associate a specific device with a specific individual undergoing treatment, permitting device tracking, prevention of cross contamination between individuals, and/or prevention of re-use of a disposable implementation of a device of the inventive concepts.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 10 provides an overview of a catheter/cannula aligned for attachment to the assembly of FIG. 9.

FIG. 11 provides examples of calculations for waveguides for use in catheters of various catheter sizes.

DETAILED DESCRIPTION

Figure 1:
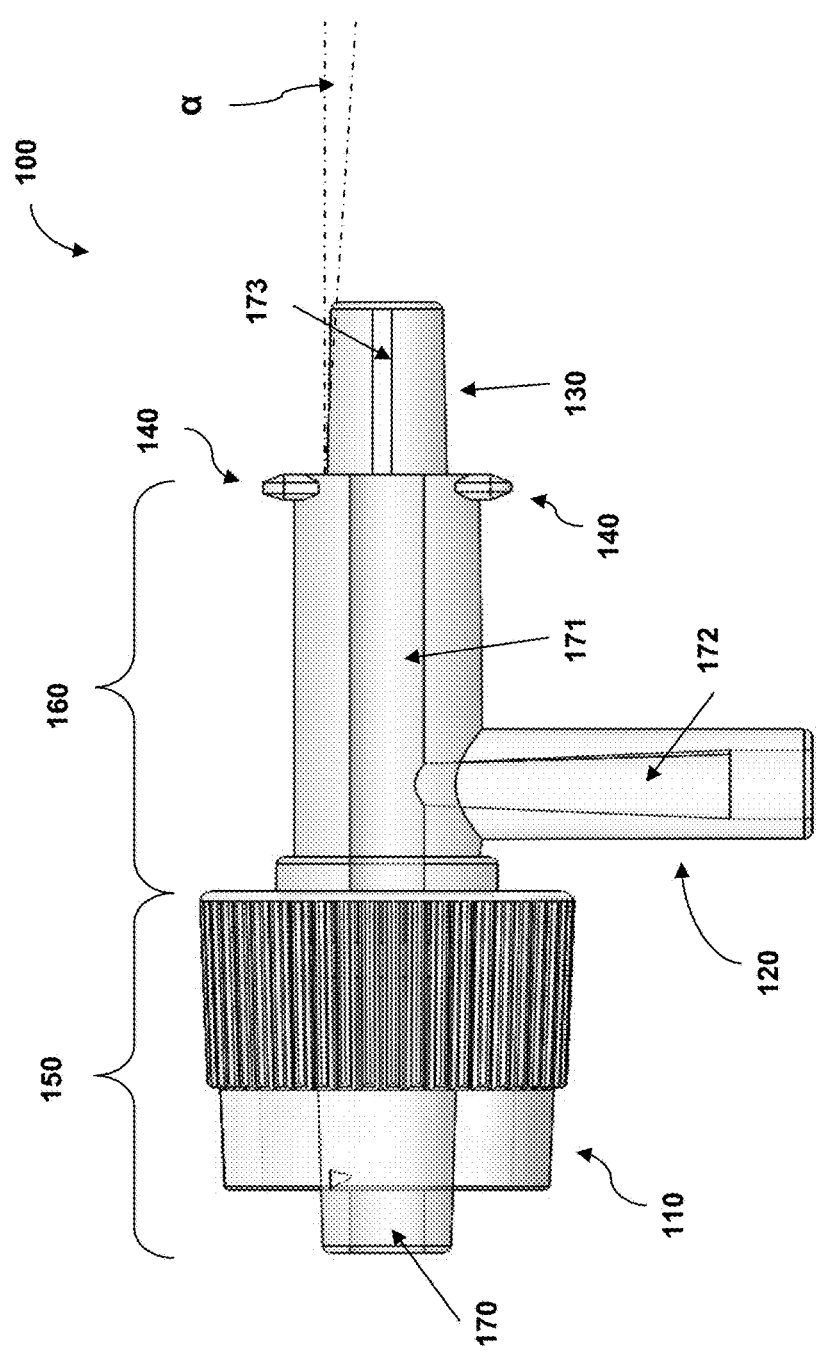
FIG. 1 provides an overview of an adapter device, according to embodiments of the inventive subject matter.

Throughout the following discussion, numerous references will be made regarding sources of electromagnetic radiation. It should be appreciated that the use of such terms is deemed to represent one or more sources configured to produce electromagnetic energy, particularly ultraviolet, visible, and/or infrared light. Such light may be coherent or incoherent. For example, a source of electromagnetic energy can include one or more of an incandescent light, a metal vapor lamp, an HID lamp, a fluorescent lamp, a laser, a gas laser, an LED laser, a light emitting diode, and/or any suitable light source. Such sources of electromagnetic energy can be configured to produce a plurality of different wavelengths, and can also include devices for distribution of electromagnetic energy (for example, fiber optic cables and their associated connectors). It should also be appreciated that such sources may utilize a variety of optical connectors, for example an SMA-905 optical fiber connector. A device of the inventive concept can be compatible with any suitable optical connector.

One should appreciate that the devices described herein provide a simple and direct means of irradiating blood and other body fluids, without the hazards associated with removal and return of fluid volumes and without the possibility of accidental transfer of potentially contaminated fluids between individuals. In addition, isolation of the optical interface from such fluids insures optimal and consistent transmission of light from the light source to the waveguide within the individual undergoing treatment, thereby providing consistent and reproducible irradiation. One should appreciate that the disclosed techniques provide many advantageous technical effects including providing an optical interface between a light/radiation source and an adapter device such that the light/radiation and an exogenous fluid can be simultaneously provided to a patient through the adapter device via a catheter while maintaining the optical interface isolated from the exogenous fluid flow, such that the light source can be simply and easily coupled and decoupled from the adapter device without requiring twisting of the adapter device or the light source fiber.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Fundamentally, embodiments of the inventive concept can be systems and devices that support optical communication or insertion of a waveguide into a vascular and/or lymphatic of an individual and connection of the waveguide to a source of electromagnetic radiation (for example, ultraviolet of visible light) via an optical interface. In such embodiments, an adapter device such as a "T adapter" can serve to support a waveguide, a connector that supports a device for accessing a venous or lymphatic space (for example a needle, cannula, or catheter), and provide a connection that supports optical interfacing with a light source. An example of an adapter device 100 according to embodiments of the inventive subject matter is shown in FIG. 1. The adapter device 100 can include a rotatable slip lock ring 110 that is compatible with commercially available Luer lock devices that are commonly utilized for venous access. The adapter device 100 can also include an exogenous fluid inlet 120, which can permit administration of fluids (e.g., pharmaceutically acceptable fluids) to an individual during irradiation. Fluids (such as saline) can be used to prevent the formation of clots during treatment. Alternatively, therapeutic fluids (for example, vitamins, cofactors, and pharmaceuticals) may be administered during irradiation via the exogenous fluid inlet 120. As shown in FIG. 1, embodiments of the adapter device 100 can include a modified tapered male terminus 130 and protrusions 140 configured to capture a rotatable locking ring, forming a "reverse" Luer lock or connector. As illustrated in FIG. 1, the protrusions 140 can be "wings" or "tabs". In other embodiments, the protrusions 140 can include threads that match with the threaded interior of a locking ring. The adapter device 100 can be made of medical grade polymers providing a suitable rigidity of construction. Examples of suitable medical grade polymers can include polyacrylates, polyamides, polycarbonates, and combinations thereof.

In embodiments, the taper angle α of tapered terminus 130 can be between 1 and 10 degrees from horizontal. In preferred embodiments, the taper angle α of tapered terminus 130 is between 2 and 6 degrees. In still more preferred embodiments, the taper angle α of the tapered terminus 130 is 3 degrees from horizontal.

For the purposes of reference, the section of the adapter device 100 having the slip lock ring 110 and opening to connect to a catheter can be generally referred to as the vascular access section 150, and the section of the adapter device 100 between the vascular access section 150 and the tapered terminus 130 can be generally referred to as the central section 160. In the embodiment illustrated in FIG. 1, the protrusions 140 and the fluid inlet 120 are considered to be part of the central section 160.

As shown in FIG. 1, the adapter device 100 includes lumens 170-173. Lumens 170-172 are in fluid communication with one another. In embodiments, lumens 170 and 171 are the same lumen extending through the central section 160 and vascular access section 150. The diameter of lumens 170-172 can be standard sizes, configured to fit exogenous fluid sources and/or the largest lumen diameters of attached catheters/cannula. Lumen 173 is aligned axially with, but fluidly isolated from, lumens 170, 171.

In embodiments of the inventive concept the tapered male terminus 130 may be essentially solid or filled with solid material at final assembly. As will be described below, this "reverse Luer" connector can be utilized to connect with a light source. Use of a solid tapered male terminus 130 can advantageously isolate an optical interface of a device of the inventive concept from fluids, reducing light losses due to scattering and providing a consistent light intensity during use. Of course, it should be recognized that all medically acceptable couplings are also expressly contemplated for use herein. While it is generally preferred that the fluid (and other connectors) are Luer-type connectors, it should be appreciated that all other types of medically acceptable connectors, and particularly tapered connectors are also deemed suitable for use herein. Thus, the term "Luer" should not be understood to be limited to a specific type of connector, but as an example of medically-acceptable connectors (most typically tapered connector with retention and/or locking element).

Figure 2:
FIG. 2 provides an isometric view of the adapter device of FIG. 1 and the assembly of a waveguide and sheath.

As shown in FIG. 2, the adapter device 100 of the inventive concept can include a waveguide 210 (for example, an optical fiber) and a sheath 220. The waveguide 210 can be placed within the sheath 220, and can be held in place using a biocompatible adhesive or filler, shown collectively as sheathed waveguide 300 in FIG. 3. In such an embodiment the sheath 220 can serve to guide and protect the waveguide 210. The sheath 220 can be constructed of any suitable material that provides the requisite strength and biocompatibility, for example heat shrink tubing or stainless steel.

In further contemplated aspects of the inventive subject matter, the waveguide 210 may be purpose-built to accommodate one or more additional functions, including resiliency and shatter proofing. For example, the waveguide 210 may be coated or otherwise at least partially coupled (e.g., adhesively coupled) to a polymer sheath that helps retain potential fragments where the waveguide is exposed to undue forces. Alternatively, or additionally, the waveguide 210 may be further encased in a secondary sheath that is mechanically more resilient (e.g., has higher modulus or hardness) than the polymer sheath. For example, a waveguide (with or without polymer sheath) may be at least partially encased in a metal tube to further protect the waveguide from mechanical impact. Thus, especially preferred exemplary waveguides may have a multi-layer configuration in which the waveguide 210 is surrounded by/bonded to a polymer sheath that is in turn disposed in a metal (e.g., stainless steel) sheath. In alternative embodiments, it is contemplated that waveguide 210 can be incorporated into adapter device 100 without a sheath.

With respect to the waveguide fiber 210, it should further be appreciated that in at least some preferred embodiments the ends of the waveguide 210 are sculpted for reduction of angular content of light, preferably to limit angular content to equal or less than 10%, more preferably to limit angular content to equal or less than 5%, and most preferably to limit angular content to equal or less than 2%.

Figure 3:
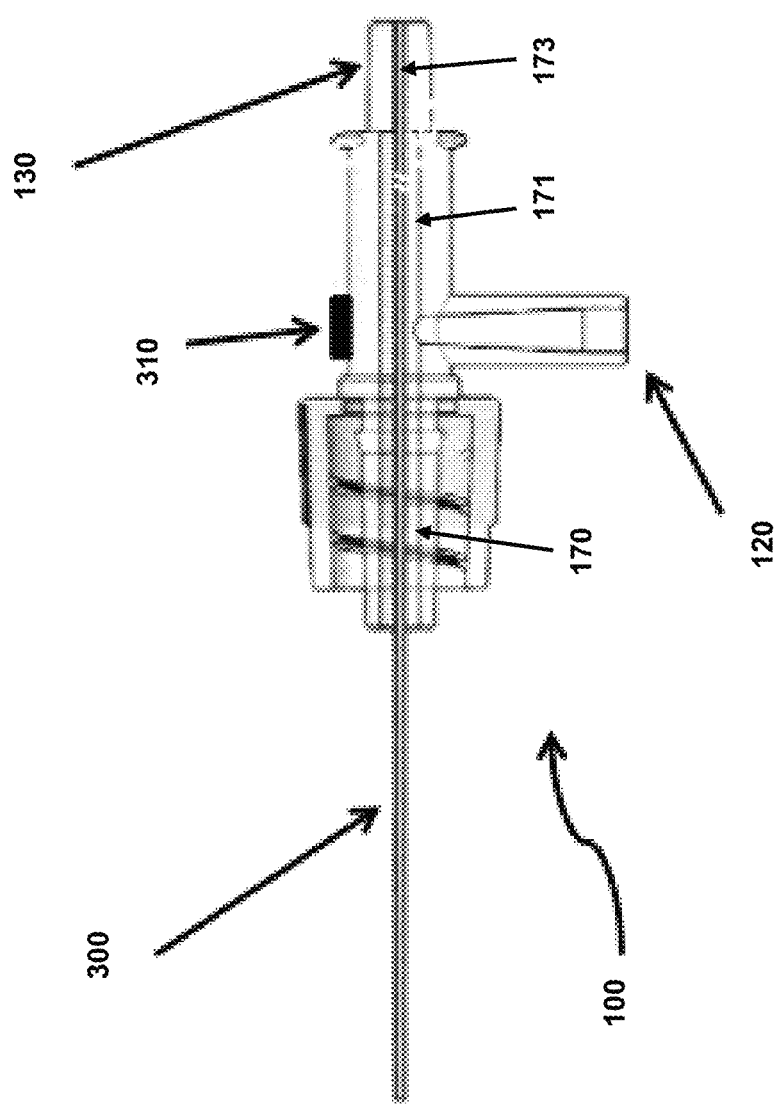
FIG. 3 provides a cross-section view of the assembled adapter device, waveguide and sheath.

FIG. 3 shows the positioning of the waveguide 210, and sheath 220 (as sheathed waveguide 300) within adapter device 100 according to embodiments of the inventive concept. As shown, the sheathed waveguide 300 can extend through a solid filler of the tapered male terminus 130 of the reverse Luer connector, protecting the optical interface at the end of the waveguide 210 from fluid contact while providing a fixed and reproducible alignment with a connector from a light source. This can be accomplished for example, via injection molding of the waveguide/sheath combination 300 into the adapter device 100 or by insertion of the waveguide/sheath combination 300 through a through-hole provided in the tapered male terminus 130 followed by the application of an adhesive. The sheathed waveguide 300 may be polished at each end to facilitate light transmission and reception. For convenience, the assembly of the waveguide 210, sheath 220, and adapter device 100 can be referred to as a dry light adapter ("DLA"). In some embodiments of the inventive concept the dry light adapter 100 is a disposable, single use item.

As illustrated in FIG. 3, the sheathed waveguide 300 is disposed within lumen 173 and passes across the length of adapter device 100, via lumens 171 and 170, extending beyond the adapter device 100. In embodiments, lumen 173 can be a "through hole" formed during the manufacturing of the adapter device 100, to which the sheathed waveguide 300 is introduced. The sheathed waveguide 300 is adhered within the lumen 173 using suitable adhesives. Suitable methods of adapter device 100 having lumen 173 within are discussed in additional detail below.

In certain embodiments, the interface end of the waveguide 300 (i.e., the end of the waveguide 300 on the terminus side of the adapter device 100 and opposite the end extending beyond the vascular access side of the adapter device 100) is flush or approximately flush with the end of the tapered terminus 130. In certain embodiments, "approximately flush" refers to the end of waveguide 300 being within 0.010 inches (0.254 millimeters) of being completely flush with the end of tapered terminus 130. In other embodiments, "approximately flush" refers to the end of waveguide 300 being within 0.005 inches (0.127 millimeters) of being completely flush with the end of tapered terminus 130. In still other embodiments, "approximately flush" refers to the end of waveguide 300 being within 0.002 inches (0.0508 millimeters) of being completely flush with the end of tapered terminus 130.

To ensure that the sheathed waveguide 300 remains aligned within the adapter device 100, the diameter of lumen 173 is preferably within 0.005 inches (0.127 millimeters) of the outer diameter of the sheathed waveguide 300. Even more preferably, the difference between the diameter of lumen 173 and the outer diameter of sheathed waveguide 300 is less than or equal to 0.003 inches (0.0762 millimeters). For example, for a sheathed waveguide 300 having an outer diameter of 0.025 inches (0.635 millimeters), lumen 173 preferably has a diameter of 0.028 inches (0.7112 millimeters).

In alternative embodiments, the sheathed waveguide 300 can be injection molded into the tapered terminus 130.

In embodiments of the inventive subject matter, adapter device 100 can include machine-readable indicia such as RFID tags, 2-dimensional barcodes, one-dimensional barcodes, etc. For example, the adapter device 100 illustrated in FIG. 3 includes an RFID tag 310. The machine-readable indicia can include information about the adapter device 100, which can include a unique adapter device identifier (e.g., for that specific adapter device 100), a part number associated with the adapter device, a lot number associated with the adapter device, an expiration date of the adapter device, adapter device specifications (e.g., size, flow capacity, compatible catheters, etc.). The machine-readable indicia can be read by corresponding devices (e.g., RFID readers, scanners, NFC interfaces, etc.), and the information provided to a system at the health care provider site (or accessible to the health care provider site). The information can be used to track the adapter device 100 via a corresponding record that can indicate to the user (e.g. administering health care professional) whether the device has been previously used, whether it has expired, and/or provide any additional warnings or instructions regarding the device. The system can provide the information via a computer terminal accessible by the user, a mobile computing device, or any other output device enabling the output of visual and/or audio information to a user. The system can include one or more computing devices that include one or more processors, non-transitory computer-readable media storing system instructions, databases storing device data, and communication interfaces enabling the exchange of data between the various components (e.g., Internet, Ethernet, cellular, WiFi, USB, HDMI, wired communications, wireless communications, etc.). In embodiments, a first scan of the machine-readable indicia on an adapter device 100 can trigger the system to create a record entry of the adapter device 100, which can include the unique identifier of the device. This record entry can be performed, for example, following a comparison of the adapter device 100's unique identifier against all present unique identifiers in the database, whereby the entry is created if no matching identifiers are found. Thereafter, a second scan of the same adapter device 100 triggers a similar comparison. Because the unique identifier for the scanned adapter device 100 exists in the database, the match can trigger the system to return a result of "previously used" for the adapter device 100 or other indication that the adapter device 100 is not fit for use and that another adapter device 100 must be retrieved for use.

The reverse Luer connector of the adapter device 100 can permit attachment to and optical communication with a light source, for example via an optical cable fitted with a suitable optical connector. Such an optical cable can be reusable. Suitable optical connections include the commonly used SMA-905 connector, however it should be understood that an adapter device 100 can be configured to interface with a wide variety of suitable optical connectors. In some embodiments of the inventive concept a reverse female Luer to optical connector adapter may be interposed between an adapter device 100 and an optical connector, permitting a single type of adapter device 100 to connect with a variety of different light sources via the use of different adapters.

Figure 4:
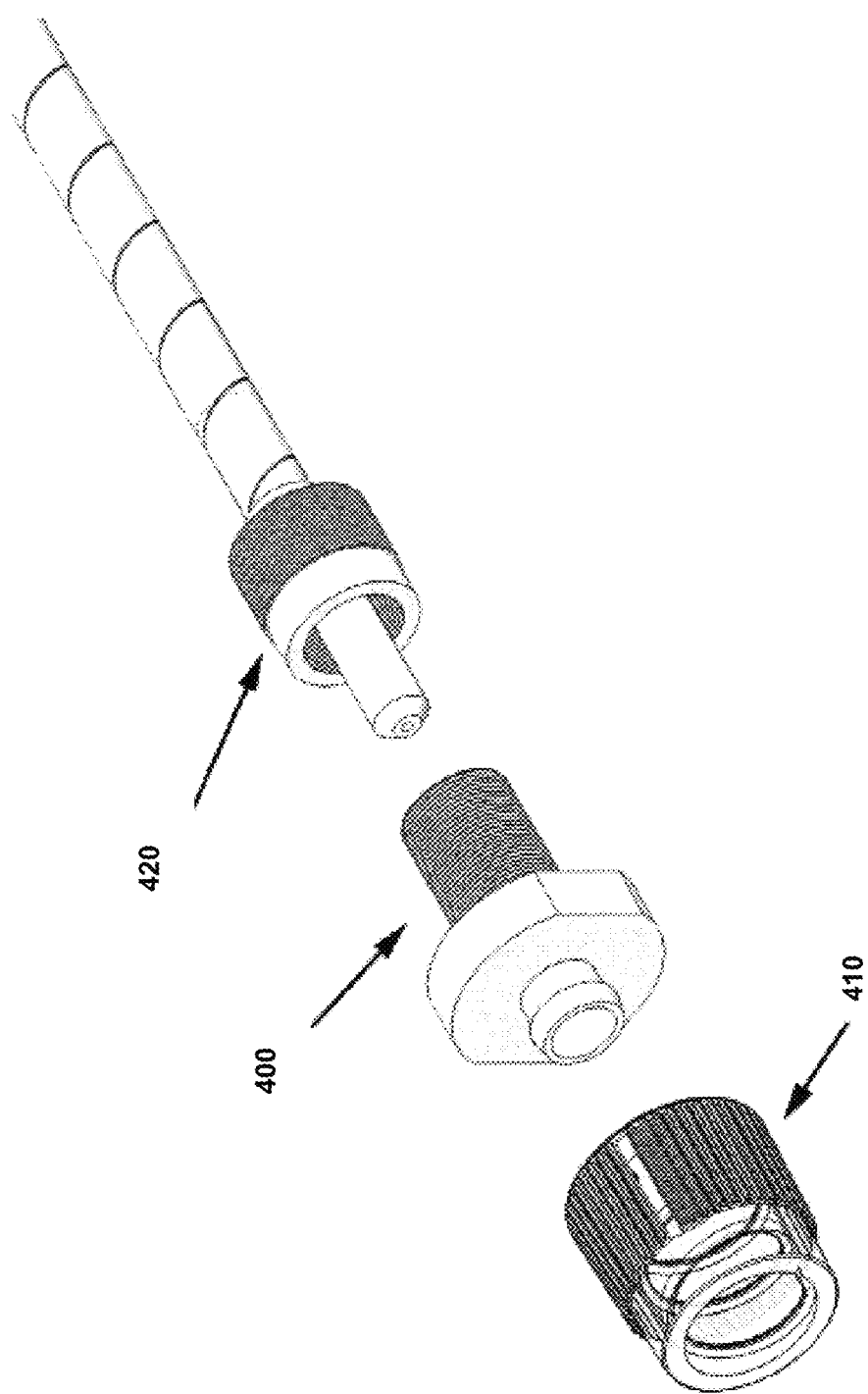
FIG. 4 provides a view of a slip lock ring, optical connector adapter and optical cable separately, aligned for assembly.

FIG. 4 shows an example of an optical connector adapter 400. The optical connector adapter 400 illustrated in FIG. 4 is a reverse female Luer to optical connector, in this instance configured for an SMA-905 optical connector, along with a typical SMA-905 terminated optical cable 420 from a light source (not shown). The optical cable 420 can include a waveguide (e.g. optical fiber) of its own used to propagate the light or other radiation from the light source to the end of the optical cable 420 and, to the waveguide 210 of the adapter device 100 when aligned via the optical connector adapter 400. Such an adapter 400 can include a slip lock ring 410, such as a Luer locking ring, that permits it to be attached securely to the protrusions 140 of the adapter device 100, such as the wings 140 of a reverse Luer connector of a dry light adapter 100 such as that shown in FIGS. 1 and 3.

Figure 5:
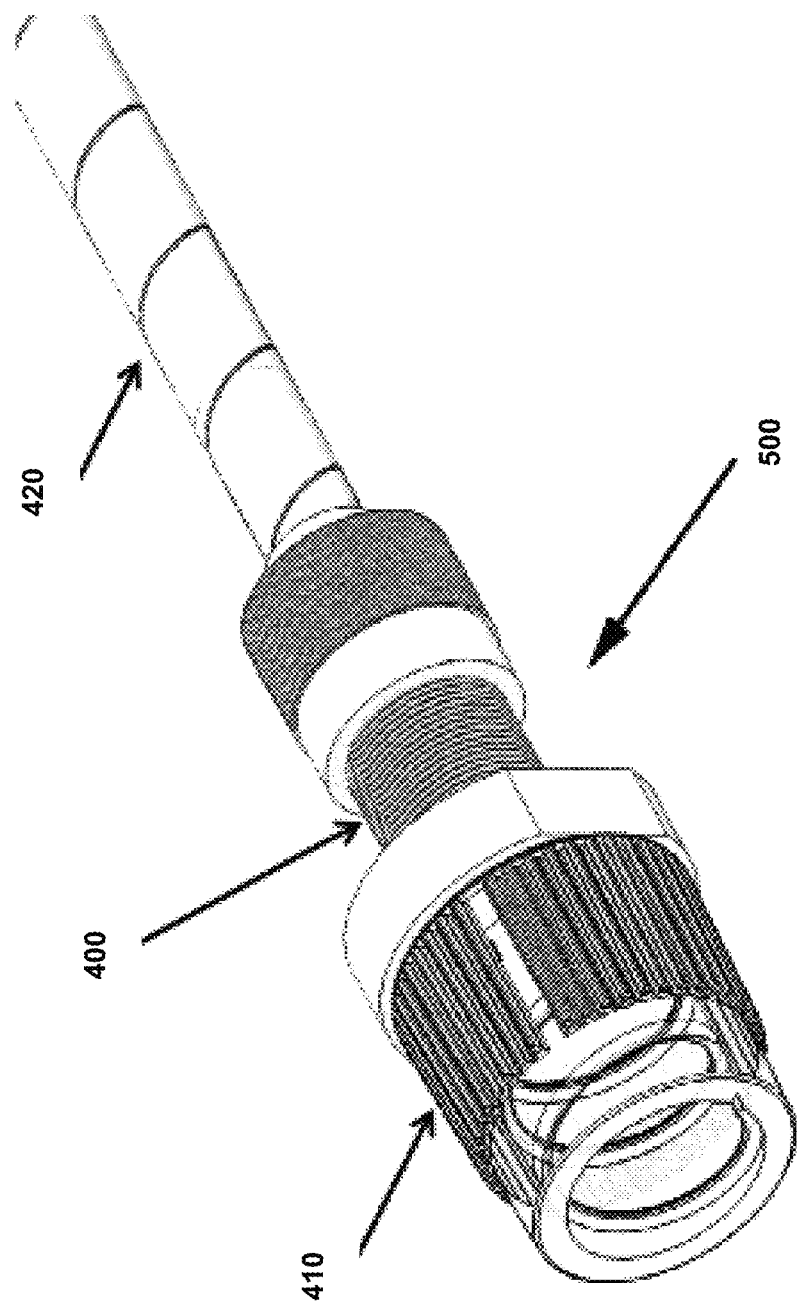
FIG. 5 provides an assembled view of the components of FIG. 4 as a patient cable.
Figure 6:
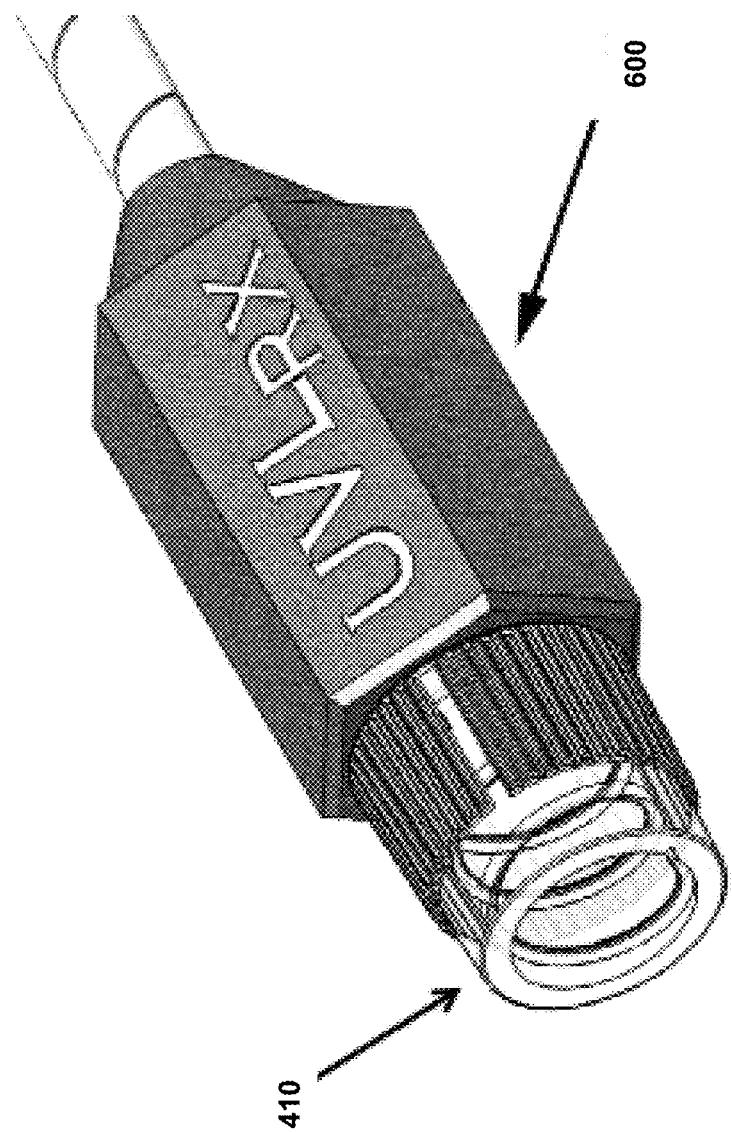
FIG. 6 illustrates the patient cable of FIG. 5 with an overmold.

FIG. 5 illustrates how the slip lock ring 410, the optical connector adapter 400 and the SMA-905 terminated optic cable 420 from a light source can be assembled. It should be appreciated that the use of an alternative optical connector adapters 400 (e.g., alternative reverse-female Luer adapters) readily permits a single type of adapter device 100 with a differently terminated optical cable 420. Such an assembly of slip lock ring 410 (of the optical connector adapter 400), optical connector adapter 400, and source optical cable 420 can be referred to as a patient cable 500. Since patient cable 500 is not in contact with a patient or patient-associated fluids it may be re-used. Such a patient cable 500 may also include power sources and/or readers for machine readable indicia (such as RFID 310) that may be incorporated into an adapter device 100. In embodiments of the inventive concept, a portion of the terminus of the patient cable can be covered with an overmold 600, as shown in FIG. 6. As illustrated in FIG. 6, the slip lock ring 410 remains external to the overmold 600. In these embodiments, it is contemplated that the overmold 600 can include a device (e.g., a battery or other power source) for energizing and/or obtaining data from machine readable indicia (such as RFID 310 illustrated in FIG. 3) included in an adapter device 100. For example, in some embodiments of the inventive concept such an overmold 600 may include a device (e.g. battery or other power source) for energizing RFID 310.

Figure 7:
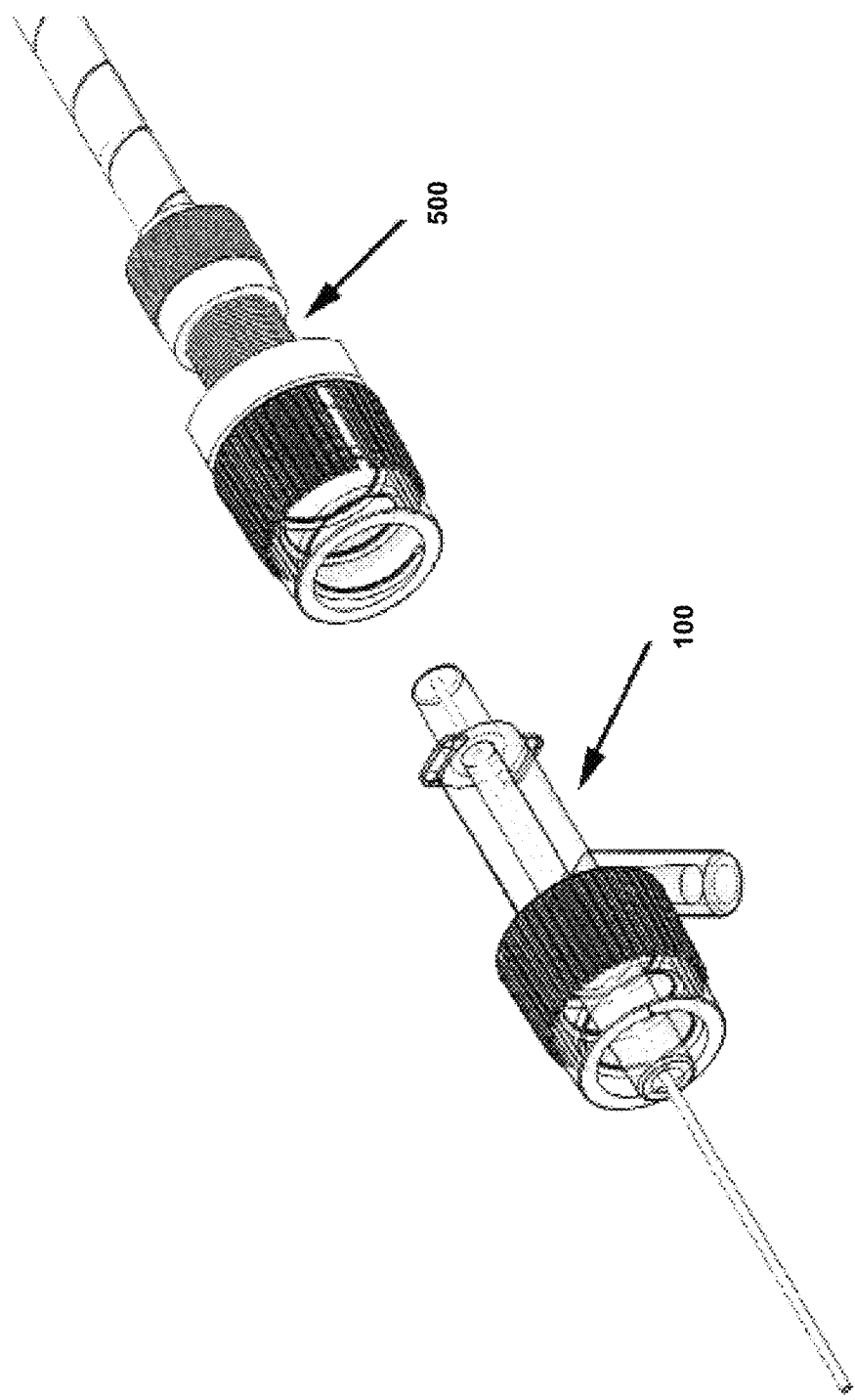
FIG. 7 provides an overview of an adapter device and patient cable aligned for coupling.
Figure 8:
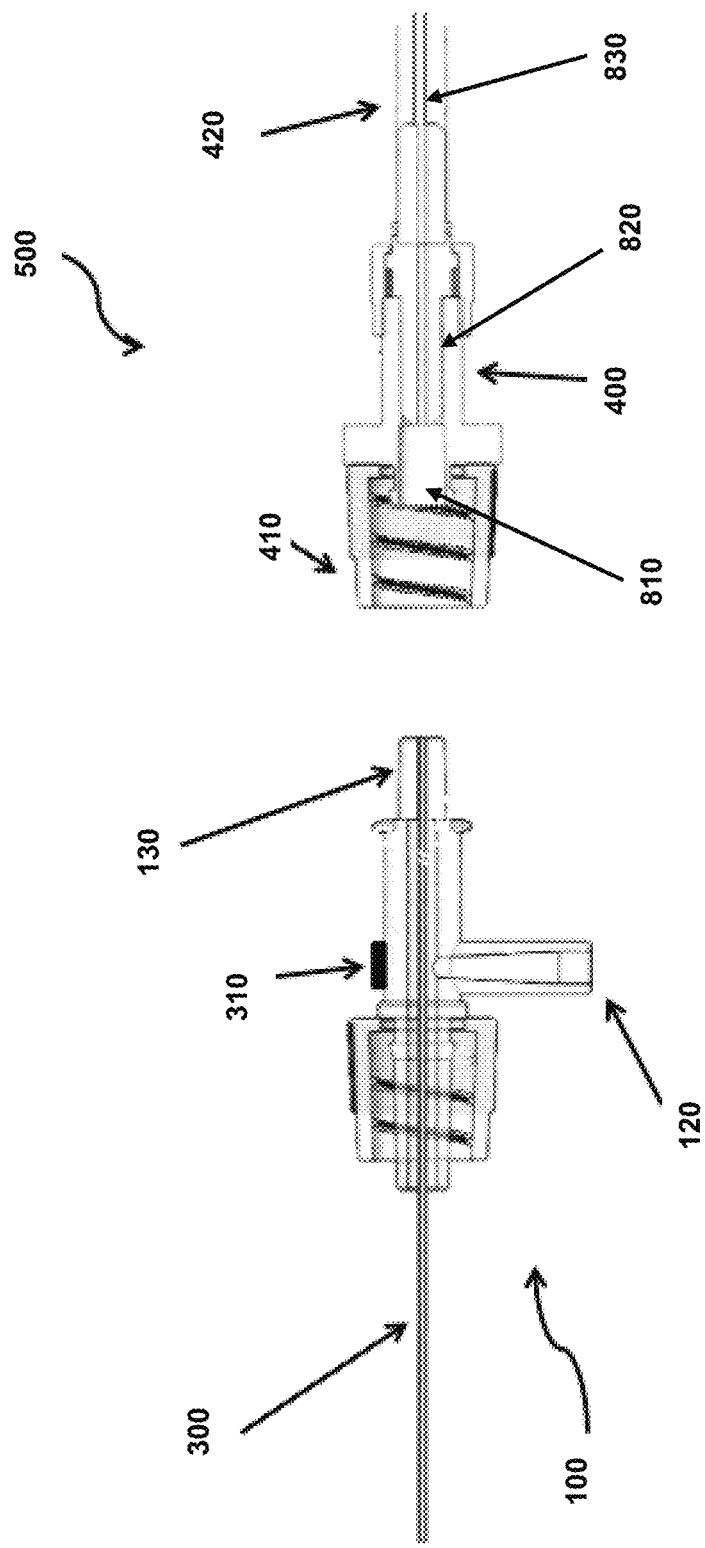
FIG. 8 provides a cross-section view of the aligned adapter device and patient cable of FIG. 7.

FIG. 7 shows an external view the alignment and orientation for coupling of an adapter device 100 to a patient cable 500. The tapered terminus 130 of the adapter device 100 provides alignment of the polished end of the waveguide 210 (of sheathed waveguide 300) with the optical fiber(s) of the patient cable 500. A detailed illustration of this alignment is shown in FIG. 8. FIG. 8 shows a cross section of adapter device 100 and patient cable 500 (i.e., the optical connector adapter 400 and its slip ring lock 410, and the source optical cable 420), aligned and oriented for coupling. As shown in FIG. 8, the source optical cable 420 includes an internal source waveguide 830 (e.g., an optical fiber), which is connected to a light source and/or radiation source (not shown).

The cross section of optical connector adapter 400 illustrated in FIG. 8 shows the internal threading of slip ring lock 410 that couples to the protrusions 140 of adapter device 100. FIG. 8 also shows a tapered internal cavity 810 that receives the tapered end 130 of the adapter device 100 and an internal interface cavity 820 that receives the male member of the source optical cable 420 (shown as already inserted in FIG. 8).

The taper of internal cavity 810 follows the taper of tapered end 130 such that the tapered end 130 fits into the cavity 810 securely without lateral movement. In embodiments, the fit of the tapered end 130 within the cavity 810 is such that the tapered end 130 is held in place via a friction fit. While it is contemplated that, in alternative embodiments of the adapter device 100, the tapered end 130 and cavity 810 can include corresponding threaded protrusions to enable a screw fit, preferred embodiments of the inventive subject matter do not include the threaded coupling between the tapered end 130 and cavity 810. Thus, the tapered end 130 and cavity 810 can be coupled and decoupled without requiring a torsion or rotational force to be applied to one or more of the adapter device 100 and the patient cable 500.

Figure 9:
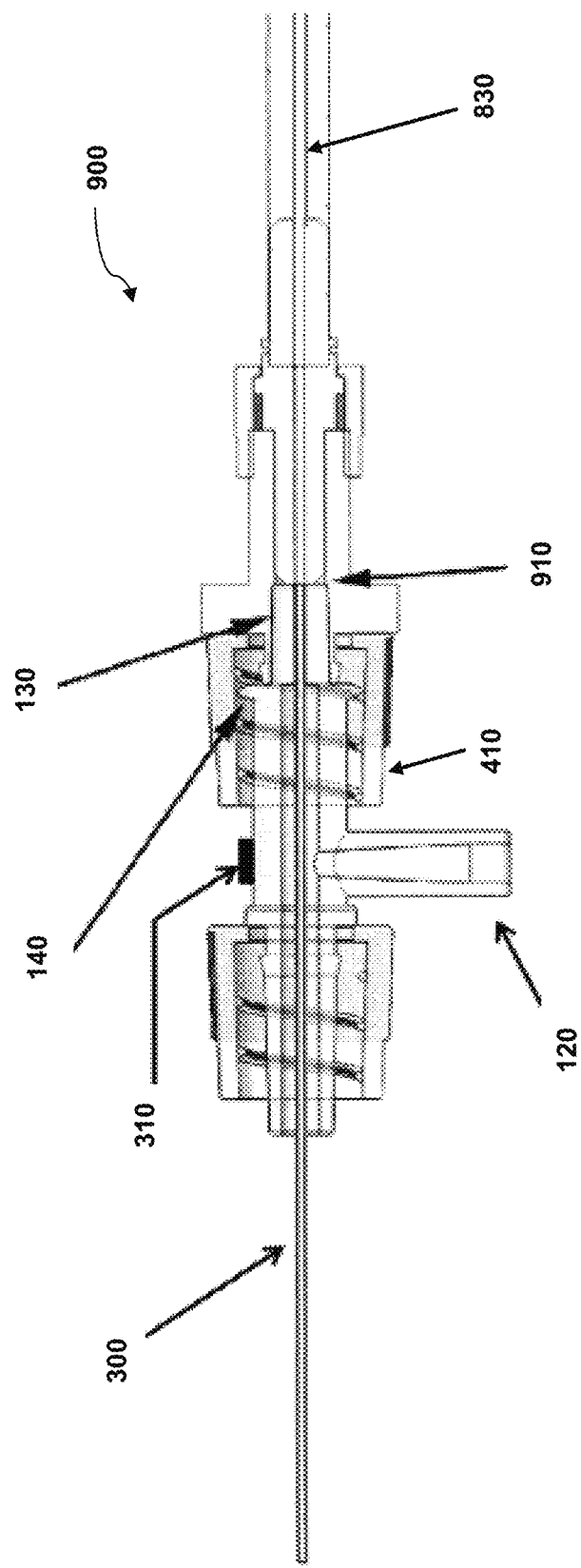
FIG. 9 provides a cross-section view of the coupled adapter device and patient cable of FIG. 8.

The internal interface cavity 820 can be shaped to fit standard optical cable fittings. In the example illustrated in FIG. 8, the interface cavity 820 is configured to fit the male member of the optical cable 420 according to the SMA-905 standard. The internal cavity 810 and the internal interface cavity 820 are shaped and aligned such that the end of waveguide 210 is optically aligned with the source waveguide 830 when the adapter device 100 is coupled with the patient cable 500, as shown in FIG. 9. For the purposes of clarity, the combined adapter device 100 and patient cable 500 are referred to collectively as assembly 900.

FIG. 9 illustrates the adapter device 100 coupled with the patient cable 500 such that tapered terminus 130 is introduced within cavity 810, and protrusions 140 are engaged with the threads of slip ring lock 410. As shown in FIG. 9, the end of the waveguide 210 is brought into optical alignment with the end of the source waveguide 830 at optical interface point 910. The optical interface point 910 can be at the shared boundary of the cavities 810 and 820. Optical alignment can be considered generally to be a distance, angle difference, or combination of distance and angle difference between the waveguide 210 and the source waveguide 830 such that light loss remains acceptable during the transfer between source waveguide 830 and waveguide 210. In embodiments, the cavities 810,820 of optical connector adapter 400 are configured to receive the tapered end 130 and source cable 420, respectively, such that the ends of waveguide 210 and source waveguide 830 are brought within 0.003 inches (0.0762 millimeters) of one another, and preferably between 0.001 to 0.003 inches (0.0254 to 0.0762 millimeters) of one another. Additionally and/or alternatively, the cavities 810,820 of optical connector adapter 400 are configured to receive the tapered end 130 and source cable 420, respectively, such that the ends of waveguide 210 and source waveguide 830 are brought within (i.e. less than or equal to) 10 degrees of parallel to one another. In other words, the long axis of the waveguide 210 and long axis of the source waveguide 830 are not offset from each other by more than 10 degrees. In embodiments, the ends of waveguide 210 and source waveguide 830 are brought within (i.e. less than or equal to) 5 degrees of parallel to one another. In still other embodiments, the ends of waveguide 210 and source waveguide 830 are brought within (i.e. less than or equal to) 2 degrees of parallel to one another.

It should be appreciated that, in embodiments of the inventive concept the optical interface (at optical interface point 910) between the waveguide 210 of the adapter device 100 and the optical fiber(s) of the patient cable 500 is isolated from patient associated fluids and does not require the use of intervening active optics (for example, a lens) for efficient light transfer. This lack of active optics simplifies design and manufacturing in addition to reducing loss of light via diffraction and scatter.

As described above, an adapter device 100 can include a slip lock ring 110 (e.g., a Luer locking ring) for attachment of a device that permits access to venous and/or lymphatic spaces. An example of this is shown in FIG. 10, which illustrates how a catheter or cannula 1000 with wings 1100 for coupling to Luer lock devices may be added to assembly 900.

It should be appreciated that, when intended for use in applications involving insertion into a catheter or cannula, the dimensions of the lumen of the cannula within which the sheathed waveguide is located drives the selection of the sheath and waveguide components of the sheathed waveguide to be used. As noted above, in embodiments it can be desirable to provide a flow of a pharmacologically acceptable fluid through a lumen of a catheter or cannula that is also occupied by the sheathed waveguide of the inventive concept. The dimensions of such catheters and cannulas is dependent on their intended use and the dimensions of the vascular space into which they are inserted. For example, a catheter intended for pediatric use in a peripheral vein can be a 22 gauge catheter, wherein a catheter used in veterinary practice or in emergency situations can be as large as 18 gauge. The waveguides and sheaths for use in such catheters can be selected so as to permit sufficient residual volume between the sheath of the waveguide and the inner wall of the lumen of the catheter or cannula to permit fluid flow. For example, the minimum flow rate through a 24 gauge catheter can be selected as a minimum desirable flow rate through a catheter or cannula with a lumen occupied by a sheathed waveguide. This flow rate can be used in combination with the size of the catheter or cannula to be used to determine the maximum acceptable diameter of the sheathed waveguide (and hence the sheath), which in turn can be used to determine the maximum acceptable diameter of the optical fiber. Examples of such calculations performed for waveguides for use in 18, 20, and 22 gauge intravenous catheters are provided in FIG. 11.

In embodiments, it is contemplated that the maximum diameter body of adapter device 100 (excluding slip lock ring 110) is less than or equal to the maximum diameter of the particular catheter to be used. Thus, in these embodiments, the diameter of the slip lock ring 110 is the largest diameter of the adapter device 100 as a whole.

Figure 12:
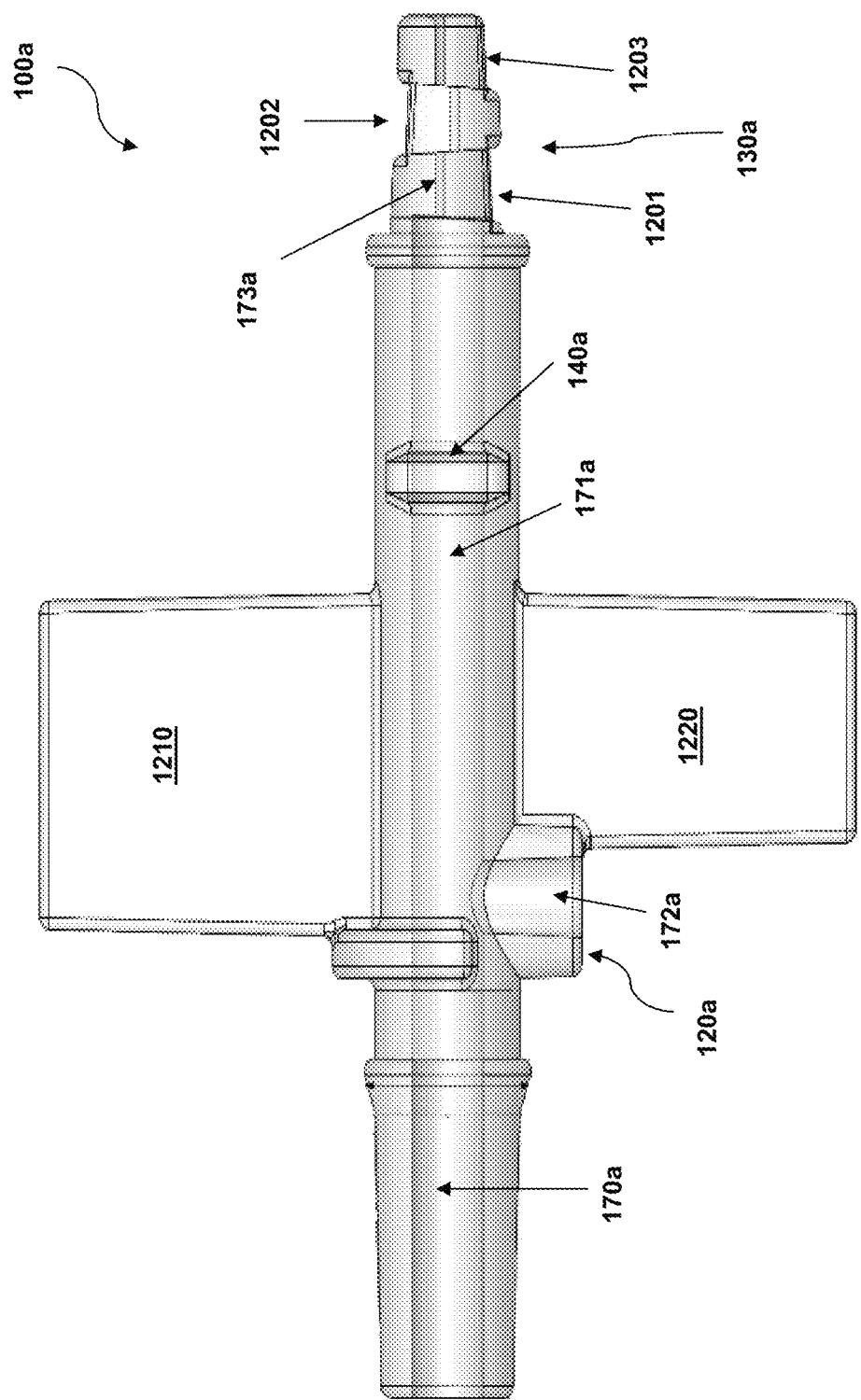
FIG. 12 is an overview of a variation of the adapter device of FIG. 1, including a segmented lumen.

It should be appreciated that lumen 173 of the inventive concept can be continuous or discontinuous (i.e. segmented). FIG. 12 shows an adapter device 100a, which is a variation of the adapter device 100 of FIG. 1. It should be noted that the labeled features of adapter device 100a having the "–a" suffix correspond to those same features in adapter device 100 of FIG. 1. For example, lumens 170a-173a of FIG. 12 correspond to lumens 170-173 of FIG. 1, and so on. Device adapter 100a is shown in FIG. 12 as having tab 140a for engagement with slip lock ring 410 of the patient cable 500. While only one tab 140a is visible in FIG. 12, is should be noted that adapter device 100a has a mirroring tab 140a on the opposite side of the device body.

As shown in FIG. 12, adapter device 100a includes a segmented lumen 173a. For the purposes of illustrating the segmenting nature of lumen 173a, the lumen is shown separated into three sections whose alignment is skewed to exaggerate the segmentation. However, it is understood that the segmented sections of lumen 173a line up to form a uniform lumen 173a through which a sheathed waveguide 300 is introduced. Additionally, while not shown in FIG. 12, the adapter device 100a also includes a slip lock ring used to secure a catheter or cannula, in the same manner of the slip lock ring 110 of adapter device 100 shown in FIG. 1.

Figure 13:
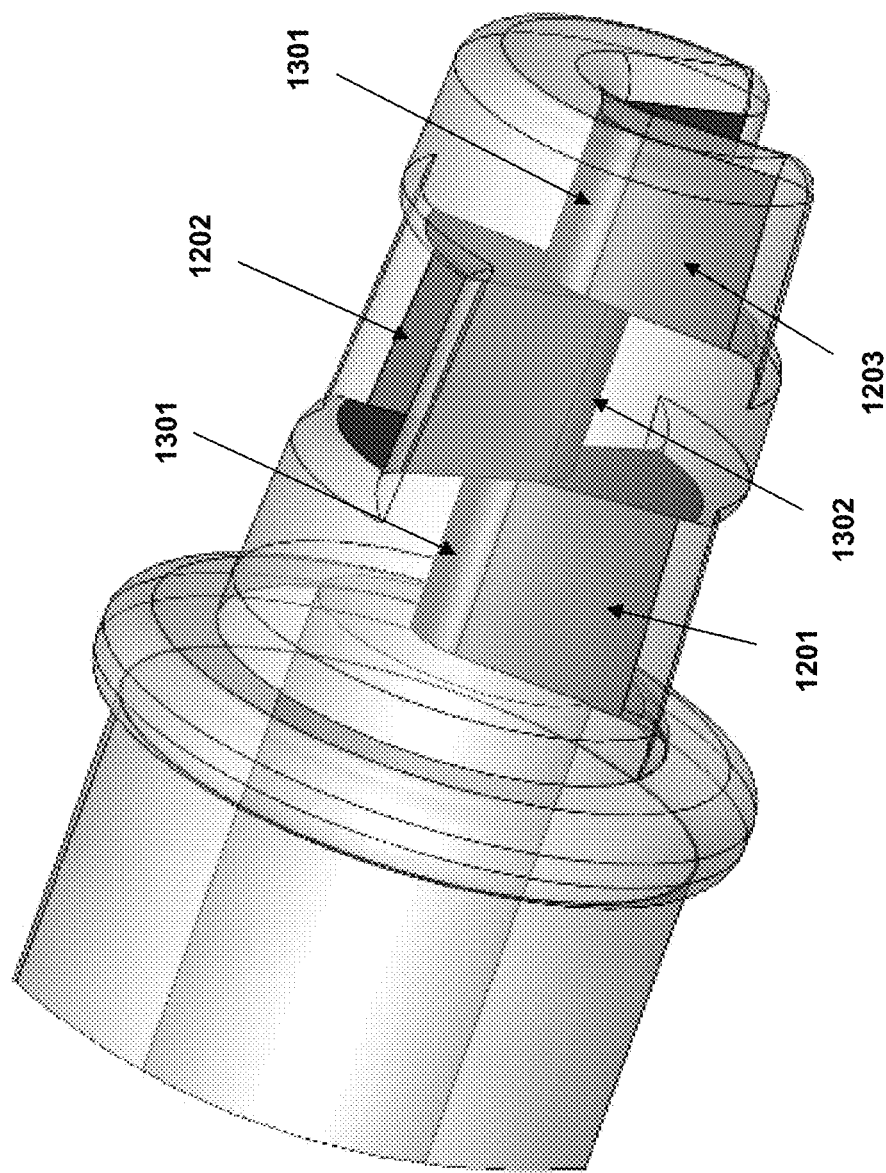
FIG. 13 is a close-up view of the tapered terminus of the adapter device of FIG. 12, illustrating the channels used to form the segmented lumen.

The segmented lumen 173a of the inventive concept can include a set of contiguous "shutoffs" or channels 1201, 1202,1203 arranged in a linear series. As shown generally in FIG. 12 and in greater in FIG. 13, at least a portion of these channels can be exposed. Such channels 1201,1202,1203 can be in rotated radially relative to one another, so that at the intersection of such rotated channels a complete encirclement occurs around the passageway (i.e. lumen 173a) thus defined. In embodiments of the inventive concept, lumen 173a can comprise a primary channel 1301 having an at least partially semicircular cross section arranged in a linear fashion with a secondary channel 1302 that has an at least partially semicircular cross section and is radially rotated by about 180 degrees relative to the primary channel, such that the region of the intersection between the primary and secondary channels 1301,1302 is circular or approximately circular. In embodiments, the lumen 173a can include additional channels offset from one another such that the region of intersection of all of the channels is circular or approximately circular. For example, three channels offset by approximately 120 degrees, four channels offset by approximately 90 degrees, etc.

It is contemplated that exposed regions of such segmented channels can be filled or partially filled during the manufacturing process. In embodiments, the sheathed waveguide 300 can be inserted into the formed lumen 173a, and the channels filled or partially filled with the waveguide 300 in place.

Figure 14:
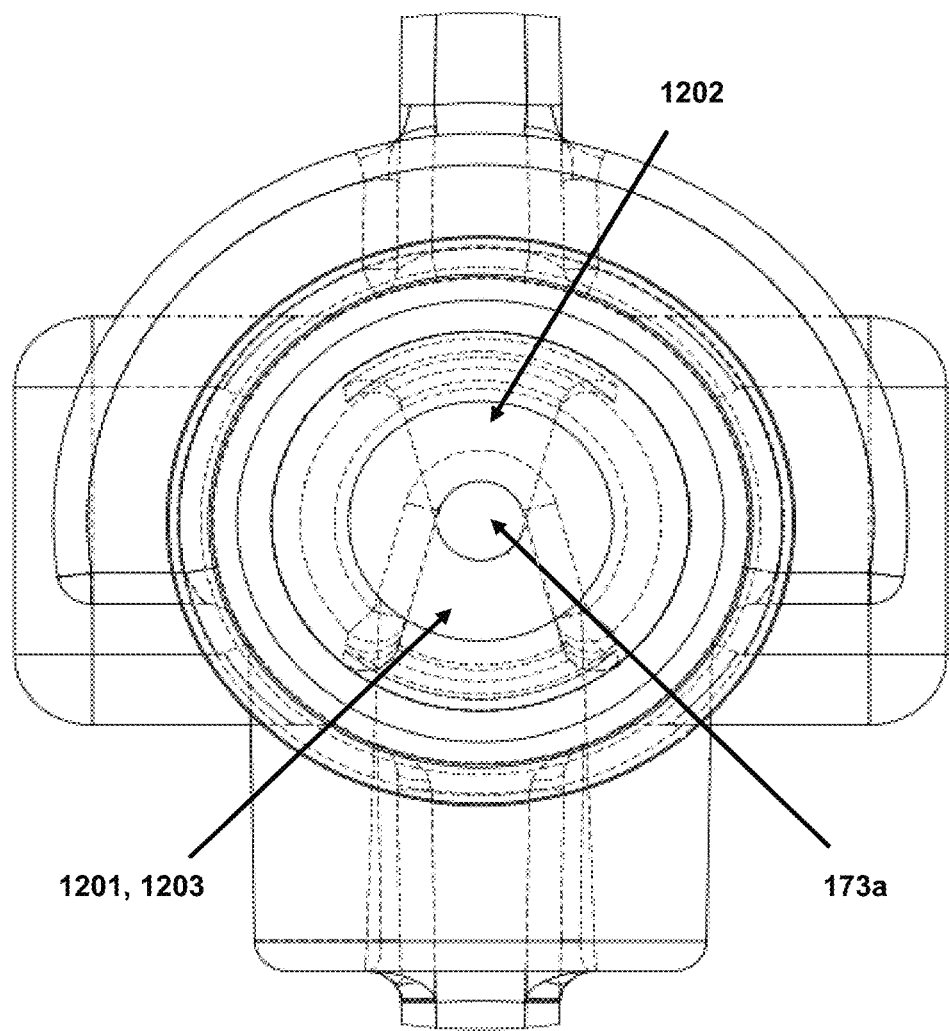
FIG. 14 is an end view of the tapered terminus of FIGS. 12-13.

FIG. 14 provides a detailed view of the adapter device 100a, as viewed from the vascular access end. As shown in FIG. 14, the lumen 173a is formed by the intersection of channels 1201,1202,1203. As channel 1203 is aligned with channel 1201, channel 1203 would be "behind" channel 1201 from the perspective of FIG. 14.

Returning to FIG. 12, the adapter device 100a is shown having an upper wing 1210 and lower wing 1220, each extending from opposite sides of the central section of device 100a.

The wings 1210,1220 are arranged on adapter device 100a such that, when the tapered end 130a is inserted into the space 810, and the slip lock ring 410 is fully secured onto the adapter 100a without interference from the wings 1210, 1220. Also, the purpose of the wings 1210 and 1220 are three-fold: they provide the healthcare provider with surfaces by which the healthcare provider can hold steady the adapter device 100a when inserting into the catheter and spinning the slip lock ring to lock the catheter 1000 and adapter device 100a in place; they likewise provide the gripping surface necessary to hold adapter device 100a steady and in place, and to prevent the adapter device 100a from spinning or pushing/torquing the catheter when attaching the patient cable 500 and locking it to the patient cable 500 with the patient cable's slip lock ring 410; and wings 1210,1220 provide a surface for securing the adapter device 100a to the patient's arm (via taping or other adhesive strip), once the whole assembly has placed together and within the patient's vein, providing strain relief In embodiments, wings 1210,1220 are a part of the single injection mold, and are of the same material as the rest of the body of the adapter device 100a, which is typically a medical grade polymer that is suitably stiff or rigid. Suitably stiff or rigid medical grade polymers allow the wings 1210,1200 and adapter device 100a generally to maintain the optical alignment of the waveguide 300 with the source waveguide 830 within the combined assembly for optimum optical coupling. In another embodiment, the wings 1210 and 1220 are overmolded onto the adapter device body, wherein the material of the wings 1210,1220 is a semi-rigid or flexible material. Examples of suitable semi-rigid or flexible materials can include silicon rubber, polyurethane, latex, nitrile, etc. In these embodiments, semi-rigid or flexible wings 1210,1220 providing the holding/grasping support required, but are able to conform to the shape of the patient's arm when the assembly is in place, increasing comfort and providing strain relief. In other embodiments, wings 1210,1220 can be added to adapter device 100a via a sleeve that is slipped over the body of the device adapter 100a, whereby the sleeve seats in place in the middle of the device adapter body at the corresponding location. In still other embodiments, the wings 1210,1220 can each comprise as two halves of a sleeve that can be assembled around the body of the adapter device 100*a*, and then glued together to capture the adapter device body. It is contemplated that the material, regardless of the method used to apply the wings 1210,1220 would be silicon rubber . . . in all cases, the wings could be secured using a close-fit, adhesive, ultrasonic weld, RF weld, etc, as is common in the art. In embodiments where the wings 1210,1220 are not part of the single injection mold, the wings 1210,1220 can be secured to adapter body 100*a* via methods and techniques such as close-fit, adhesive, ultrasonic welding, RF welding, etc.

Figure 15:
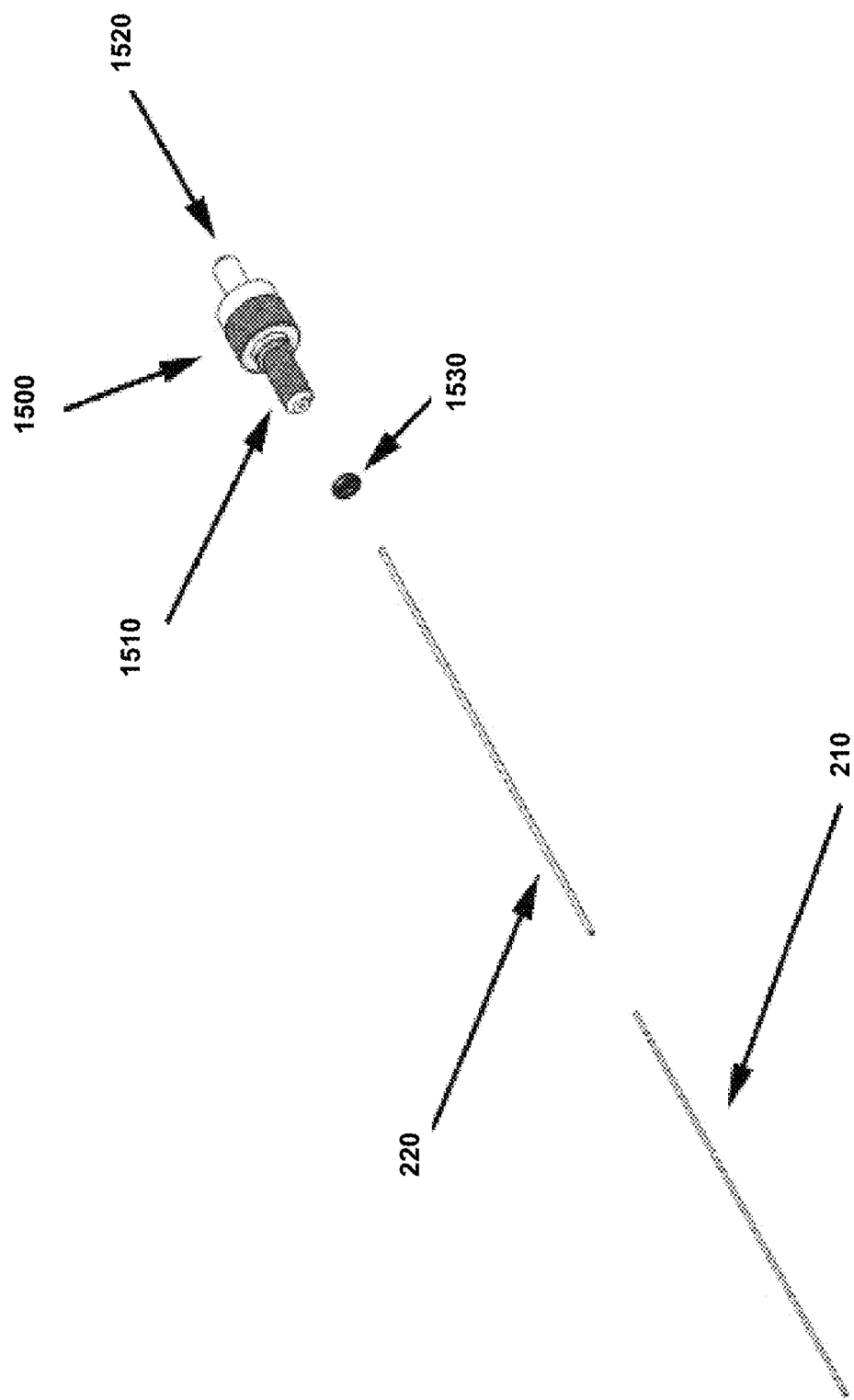
FIG. 15 is an overview of the components used to assemble an optical adapter for use in adapter device, according to alternative embodiments of the inventive subject matter.

In alternative embodiments of the inventive concept, an adapter device can receive a standard or conventional optical adapter. An example of such an embodiment is shown in FIG. 15. In these embodiments of the inventive concept, waveguide 210 for use in irradiation of blood may be adapted for use in a standard optical connector 1500 (for example, a standard SMA-905 connector) through the use of a sheath 220 and an O-ring 1530. Such a standard optical connector 1500 can include a mating end 1510 and a ferrule 1520 that provide connection with a suitably terminated optical cable from a light source. It should be appreciated that any suitable standard optical connector 1500 may be utilized.

Figure 16:
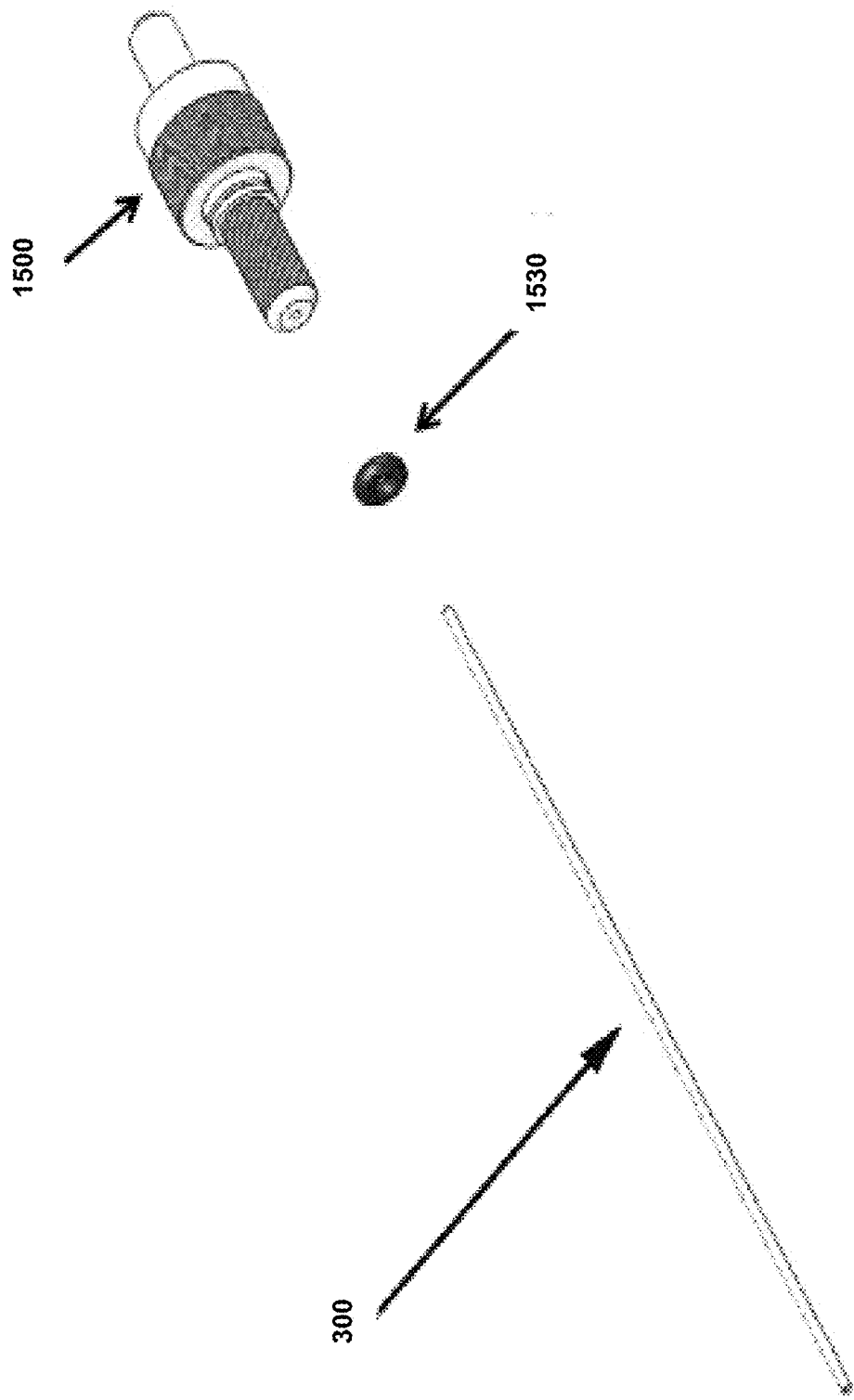
FIG. 16 provides an isometric view of the optical adapter components of FIG. 15, with the assembled sheathed waveguide.

As shown in FIG. 16 (and as illustrated in FIG. 3), the waveguide 210 can be secured within a sheath 220 to form sheathed waveguide 300. As described above, this can provide both protection for the waveguide 210 and the rigidity necessary for safe handling and accurate alignment. The waveguide 210 may be secured within the sheath 220 via an adhesive or simply held in place by close mechanical tolerances. The sheath 220 may be of any material with suitable mechanical properties and biocompatibility, for example stainless steel or heat shrink tubing.

Figure 17:
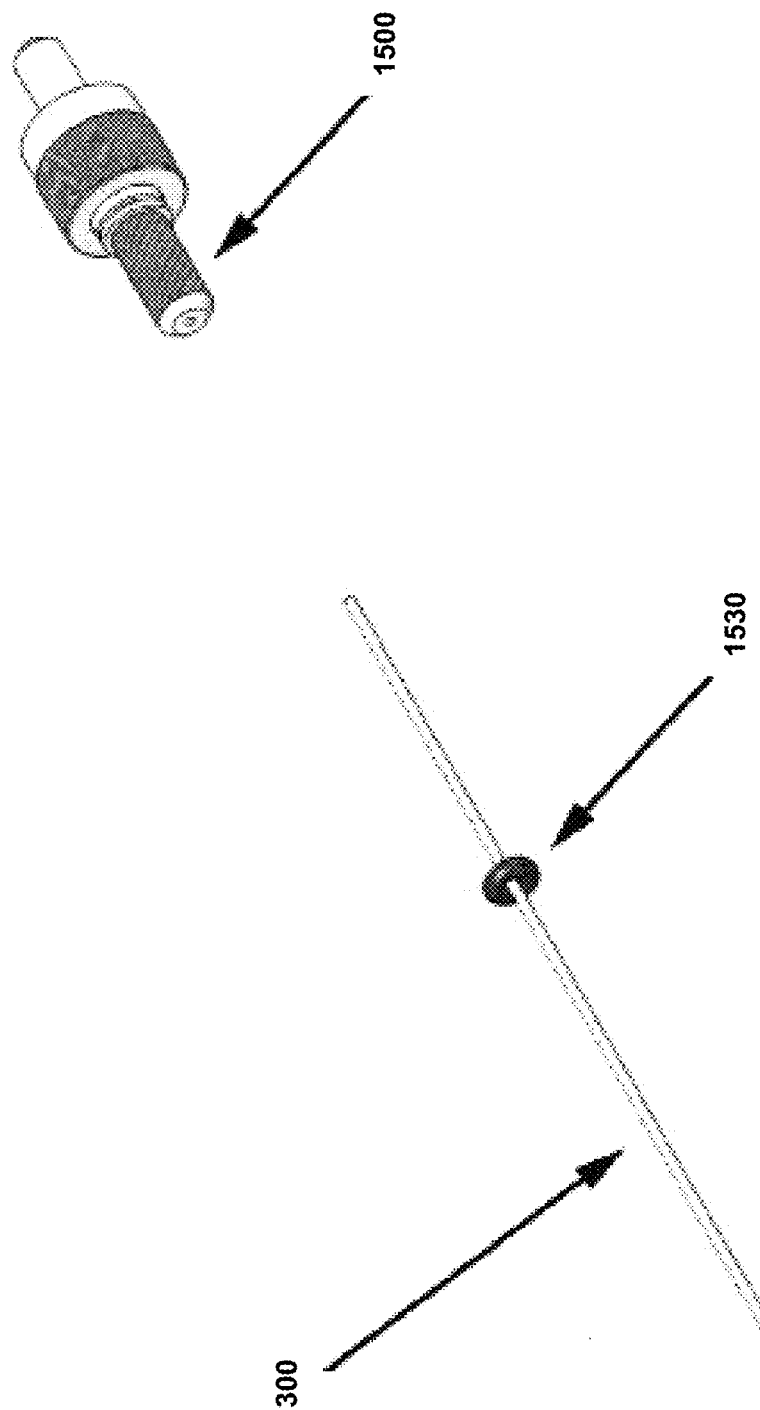
FIG. 17 provides an isometric view of the optical adapter components of FIG. 16, with the o-ring fitted over the assembled sheathed waveguide.

As shown in FIG. 17, the O-ring 1530 can be slipped over the sheath 220 during assembly, positioning the O-ring 1530 to act as a seal against the mating end of a standard optical connector 1500. The O-ring 1530 may be constructed of any suitably pliant and biocompatible material, such as silicon rubber.

Figure 18:
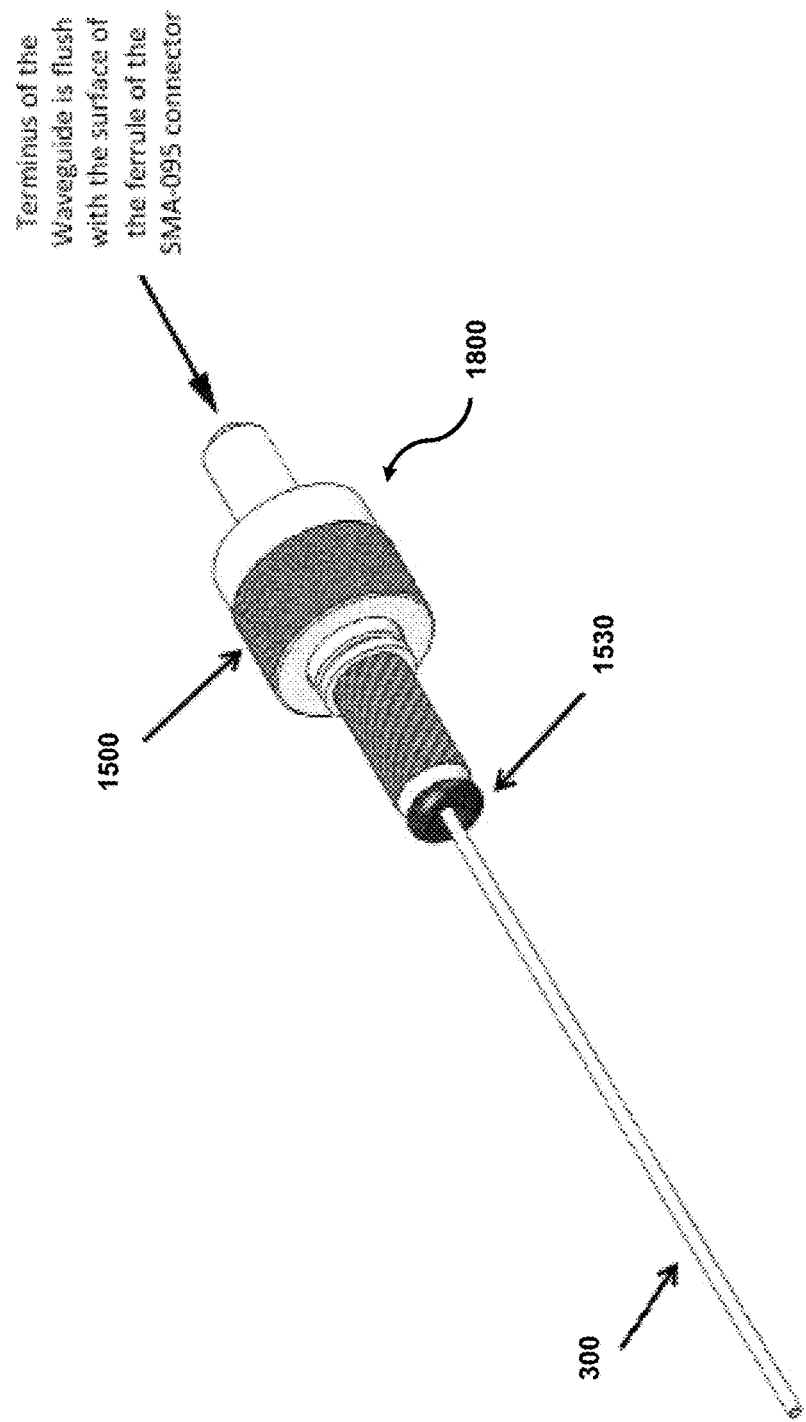
FIG. 18 provides an isometric view of the assembled optical adapter.

FIG. 18 shows a waveguide/sheath assembly 300 inserted into a standard optical connector 1500, with the O-ring 1530 positioned against the mating end of the optical connector 1500. The outer diameter of the sheath 220 of sheathed waveguide 300 and the inner diameter of the O-ring 1530 can be selected to provide a fluid-tight seal between the outer surface of the sheath 220, the mating surface of a standard optical connector 1500, and the surface of the O-ring 1530. This advantageously prevents fluids from reaching the optical interface between the waveguide and the light source. In embodiments of the inventive concept this assembly of a SMA-905 connector 1500, sheathed waveguide 300, and O-ring 1530 is referred to as a SWO assembly 1800.

Figure 19:
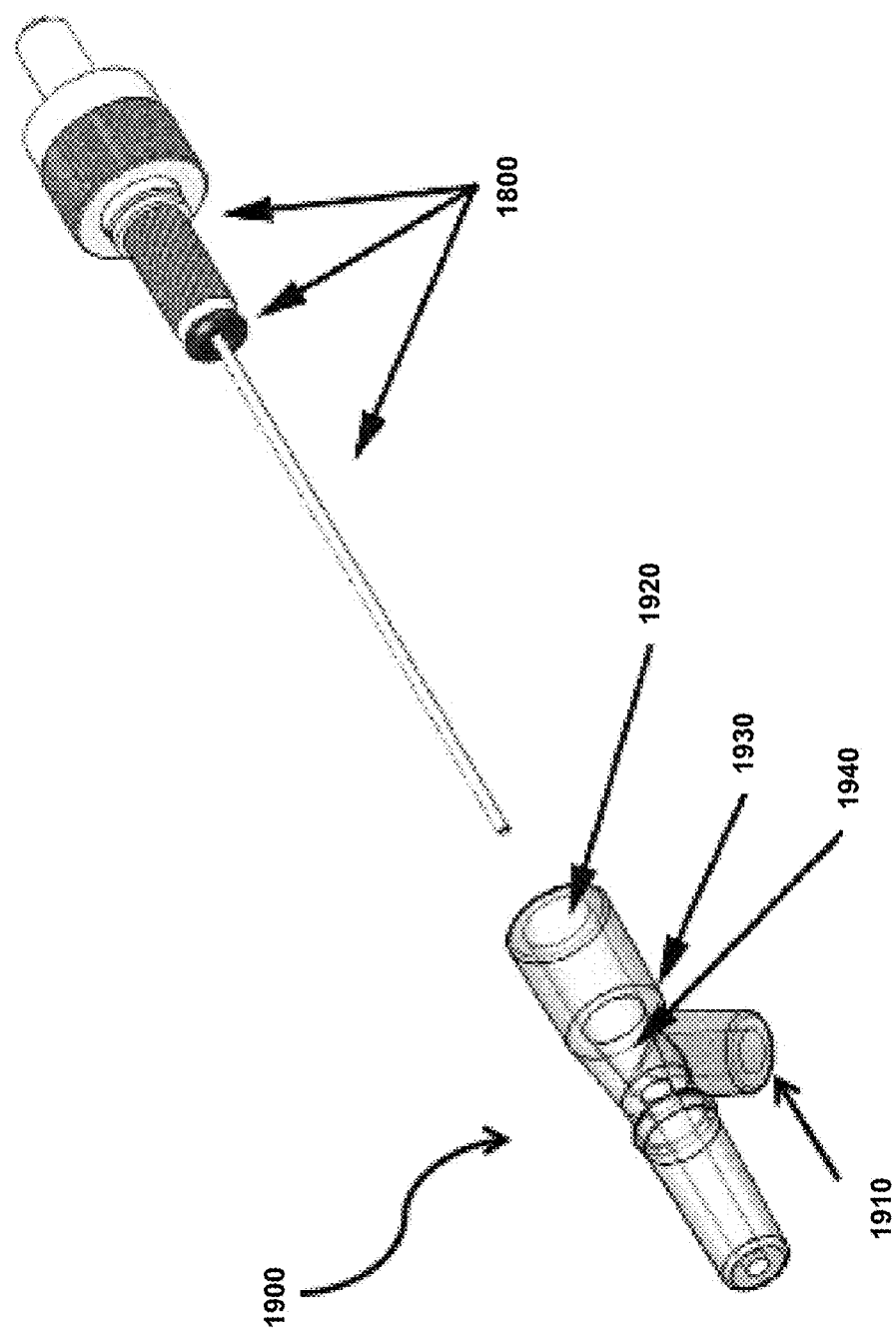
FIG. 19 shows the optical adapter of FIG. 18 aligned for assembly with an adapter device, according to the alternative embodiments of the inventive subject matter.

As shown in FIG. 19, in some embodiments of the inventive concept a SWO 1800 (or analogous assembly incorporating other standard optical connectors) can be coupled to an adapter device 1900. As with adapter device 100 described above, such adapter device 1900 can include an exogenous fluid inlet 1910. Such an adapter device 1900 can also include features that permit seating of the O-ring 1530 of a SWO assembly 1800. In the example shown in FIG. 19, adapter device 1900 includes initial recess 1920 and secondary recess 1940 portions, connected by an interposing recess transition 1930. The secondary recess 1940 can have a smaller internal diameter than the initial recess 1920, and in such embodiments the recess transition 1930 can be tapered or approximately conical. This produces a seating surface for the O-ring 1530 of the SWO 1800 upon assembly.

Figure 20:
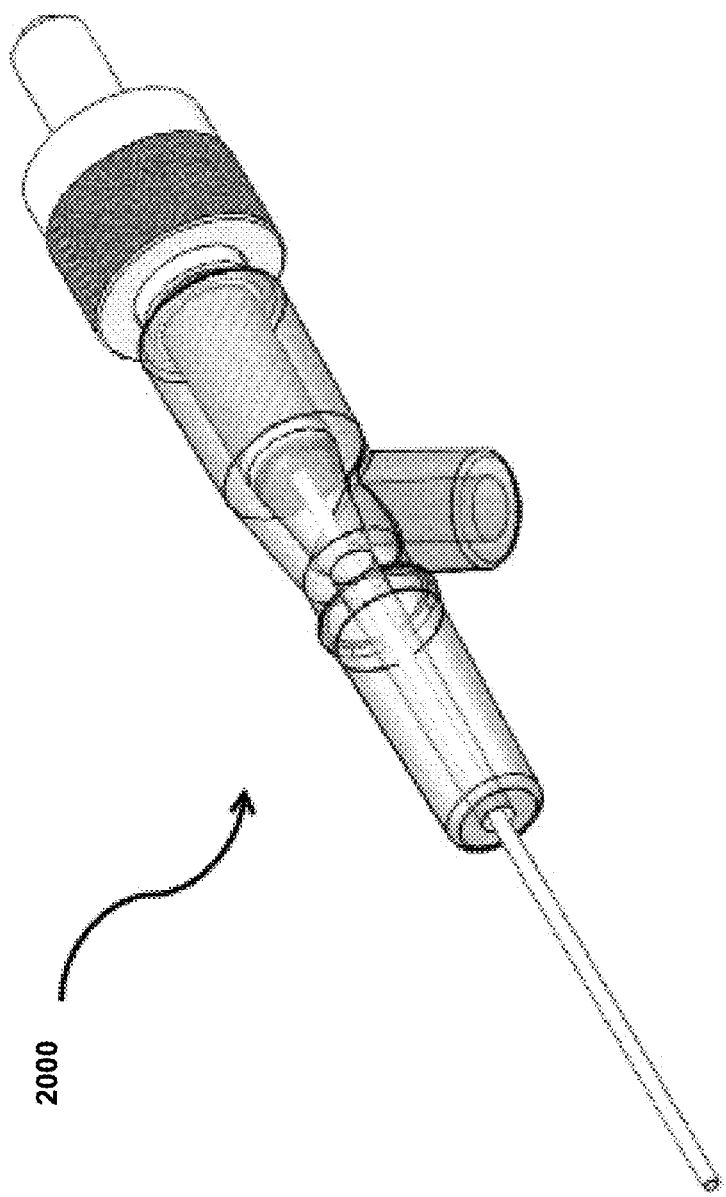
FIG. 20 illustrates the assembled dry light adapter.
Figure 21:
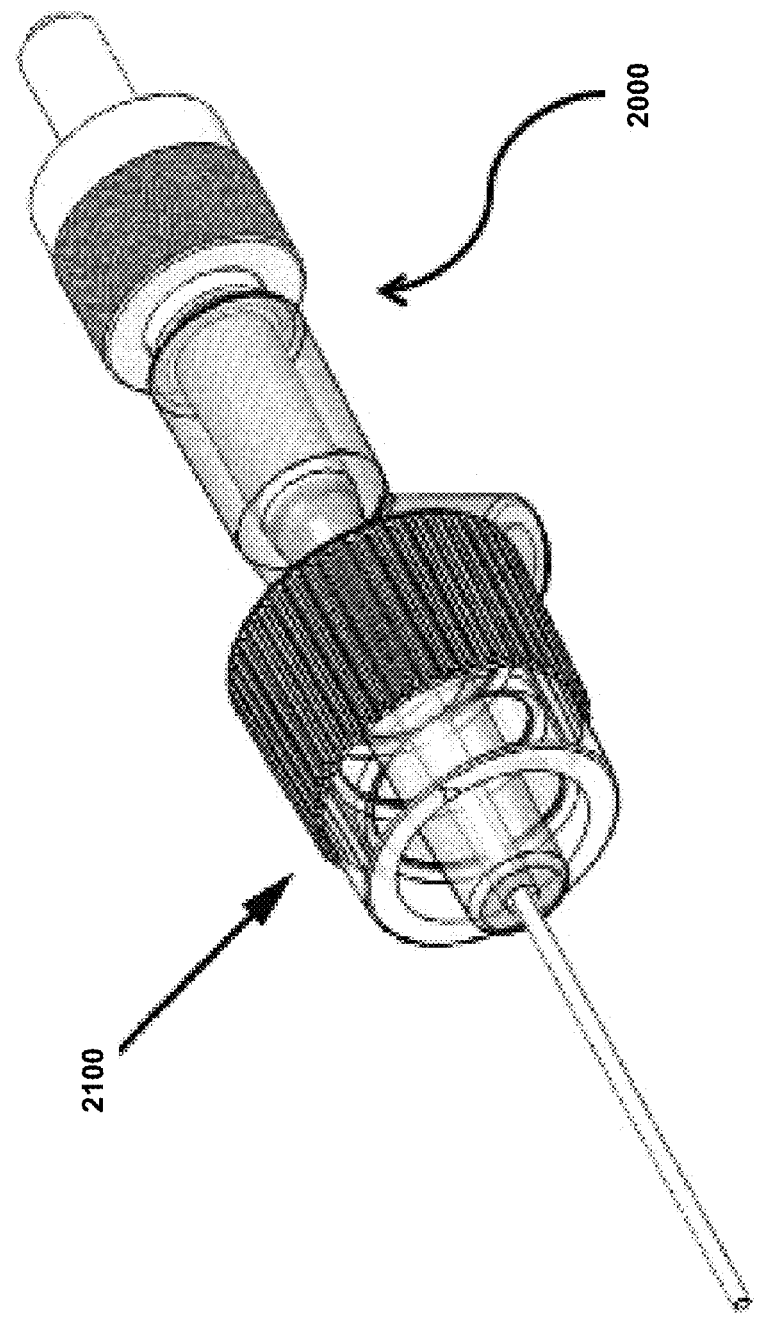
FIG. 21 illustrates the assembled dry light adapter of FIG. 20, with a slip lock ring.

As shown in FIG. 20, a SWO 1800 and adapter device 1900 can be coupled to form a "dry light adapter" 2000 with functions similar to the dry light adapter described above. It should be noted that the O-ring 1530 can form a fluid-tight seal with the interior walls of the recess transition 1930, providing further protection of the optical interface from fluids. In some embodiments of the inventive concept the SWO 1800 (or analogous device) can be secured to an adapter device 1900 using a medical grade adhesive. As shown in FIG. 21, dry light adapter 2000 can include a slip lock ring 2100 (e.g., a Luer locking ring), which permits attachment to a wide variety of medical devices used to access the venous and/or lymphatic system. Such a dry light adapter 2000 can also include machine readable indicia, as described above. As with the adapter device 100 described above, in some embodiments of the inventive concept dry light adapter 2000 can be a disposable and/or single use device.

Figure 22:
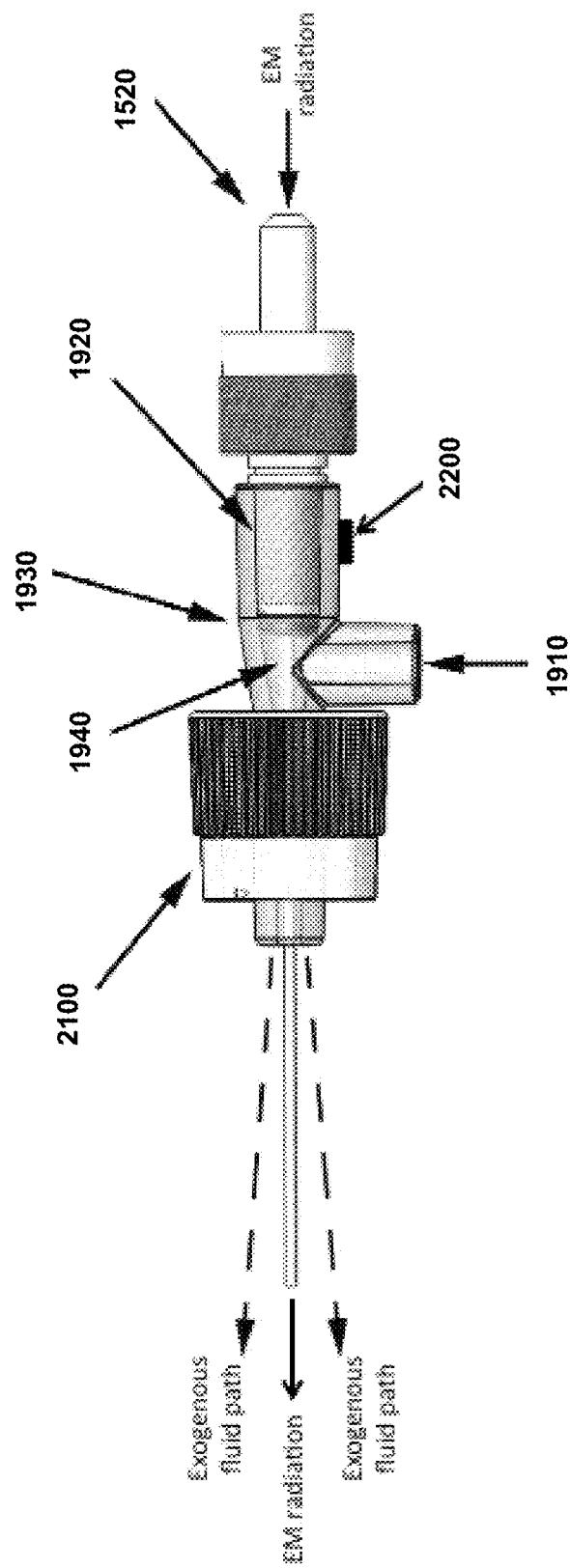
FIG. 22 provides an overview of the light and fluid paths through the dry light adapter.

Light and fluid paths through dry light adapter 2000 are shown in FIG. 22. Electromagnetic (EM) radiation from an EM or light source enters at the waveguide 300 at the interface with an optical connector. Fluids (such as saline, vitamins, cofactors, dyes, and/or pharmaceuticals) can enter through an exogenous fluid inlet. EM radiation exits from the waveguide 300 at the terminus opposing the optical connector, while exogenous fluids flow along the outside of the waveguide/sheath assembly, advantageously reducing clotting and preventing debris from entering the dry light adapter 2000. It should be noted that, despite their active introduction into the dry light adapter 2000, the optical interface is not exposed to fluids. In the illustrated example of FIG. 22, the dry light adapter 2000 is shown including RFID tag 2200.

Figure 23:
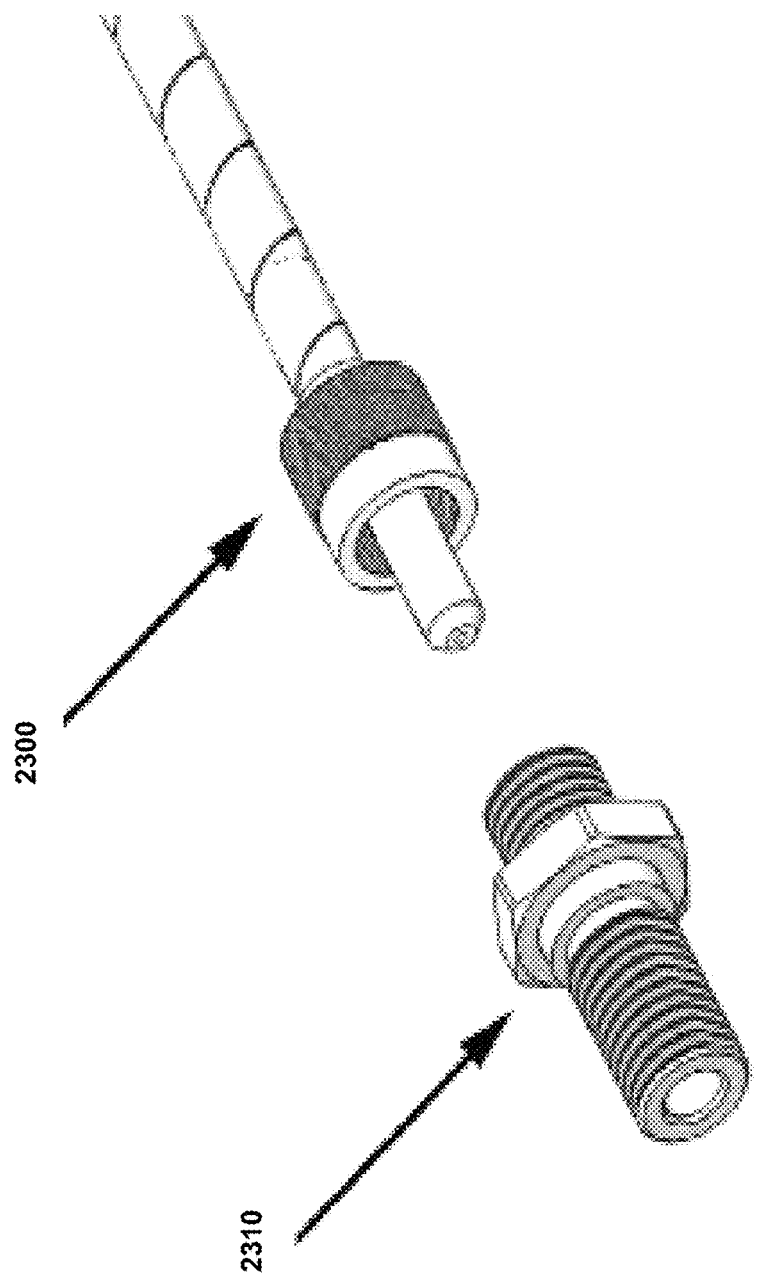
FIG. 23 shows an optical cable aligned for coupling with a bulkhead adapter.
Figure 24:
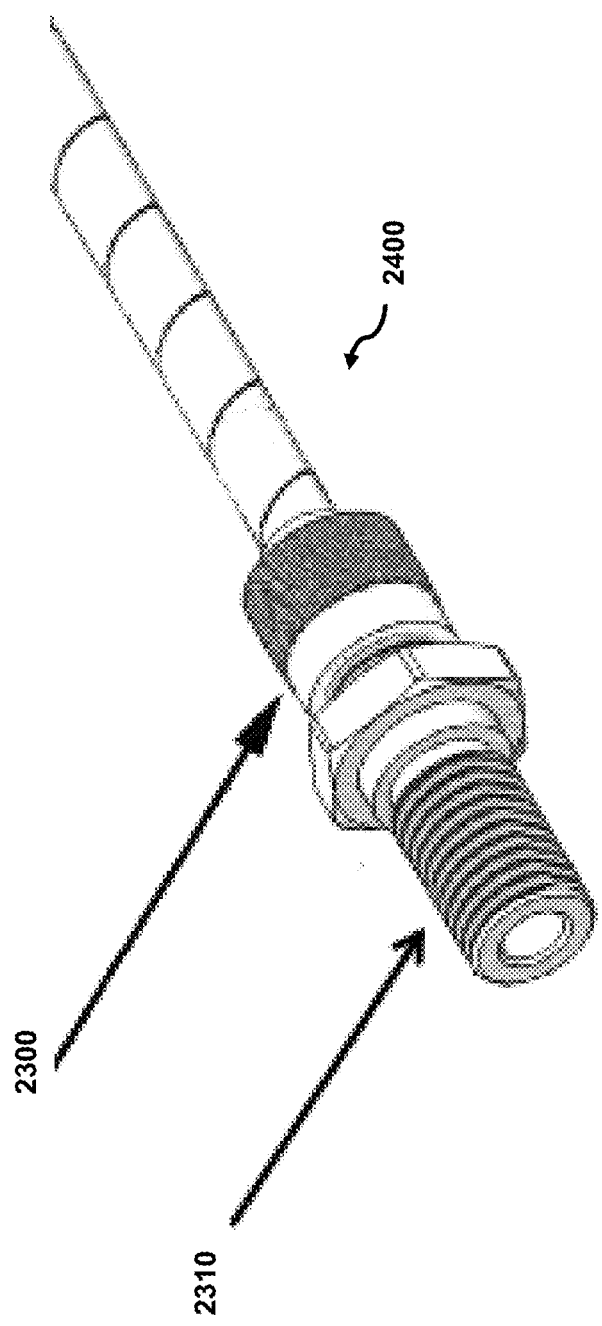
FIG. 24 shows the coupled optical cable and bulkhead adapter of FIG. 23 as an assembled patient cable.

The use of a standard optical connector in dry light adapter 2000 permits the use of conventional fiber optic cables without the need for specialized adapters. An example of this is shown in FIG. 23, which depicts a typical optical cable 2300 of the art that includes a fiber optic cable from a source that terminates in a standard SMA-905 connector that can be combined with a standard SMA-905 bulkhead adapter 2310. The combination of these off the shelf components is shown in FIG. 24, and can constitute patient cable 2400 of the inventive concept. As with patient cable 500 described above, such a patient cable 2400 can be a reusable component.

Figure 25:
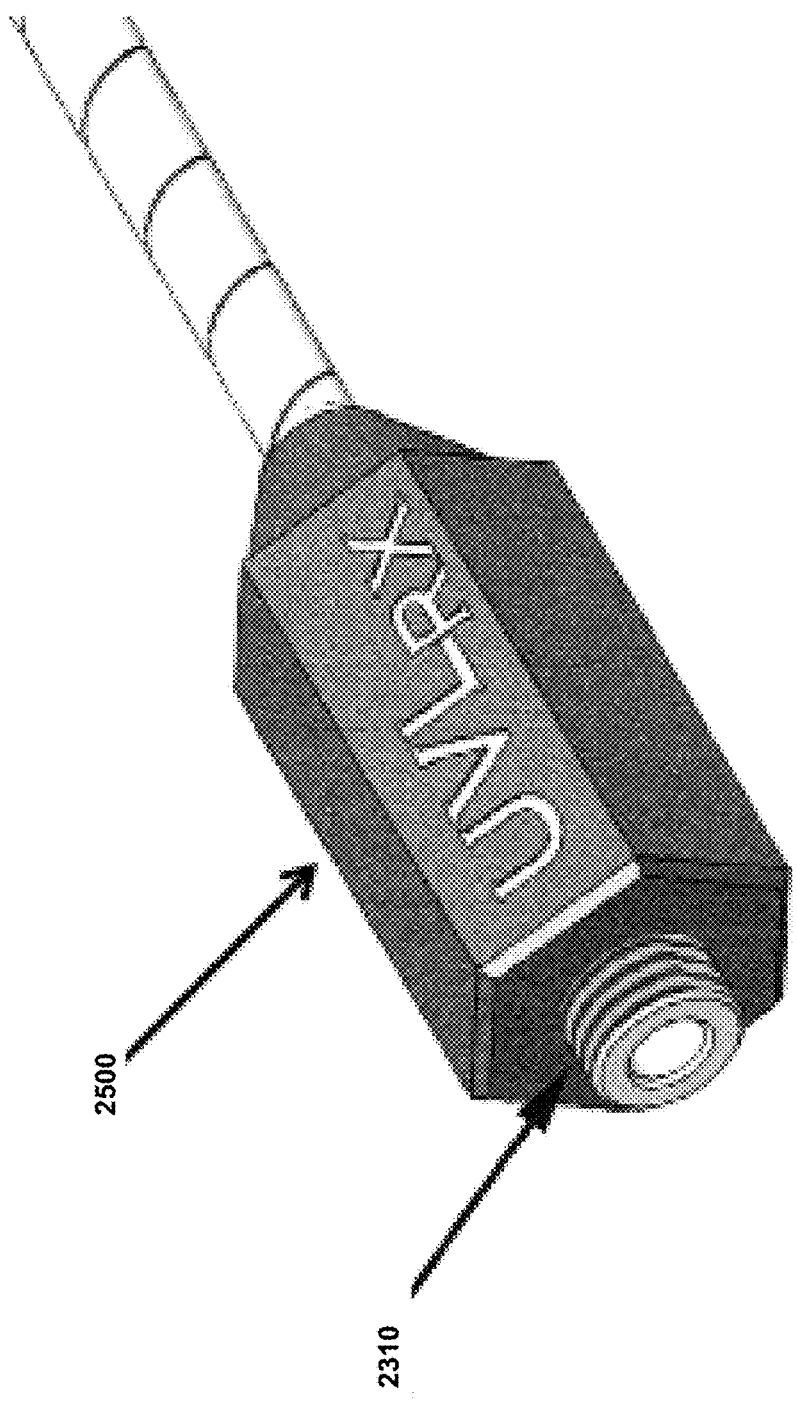
FIG. 25 illustrates the patient cable of FIG. 24 with an overmold.

As shown in FIG. 25, a terminus of patient cable 2400 (including the optical connector and at least part of the bulkhead adapter) can be enclosed in an overmold 2500. As noted for patient cable 500 above, such an overmold can incorporate an energizer and/or reader for machine readable indicia that can be incorporated into a dry light adapter 2000.

Figure 26:
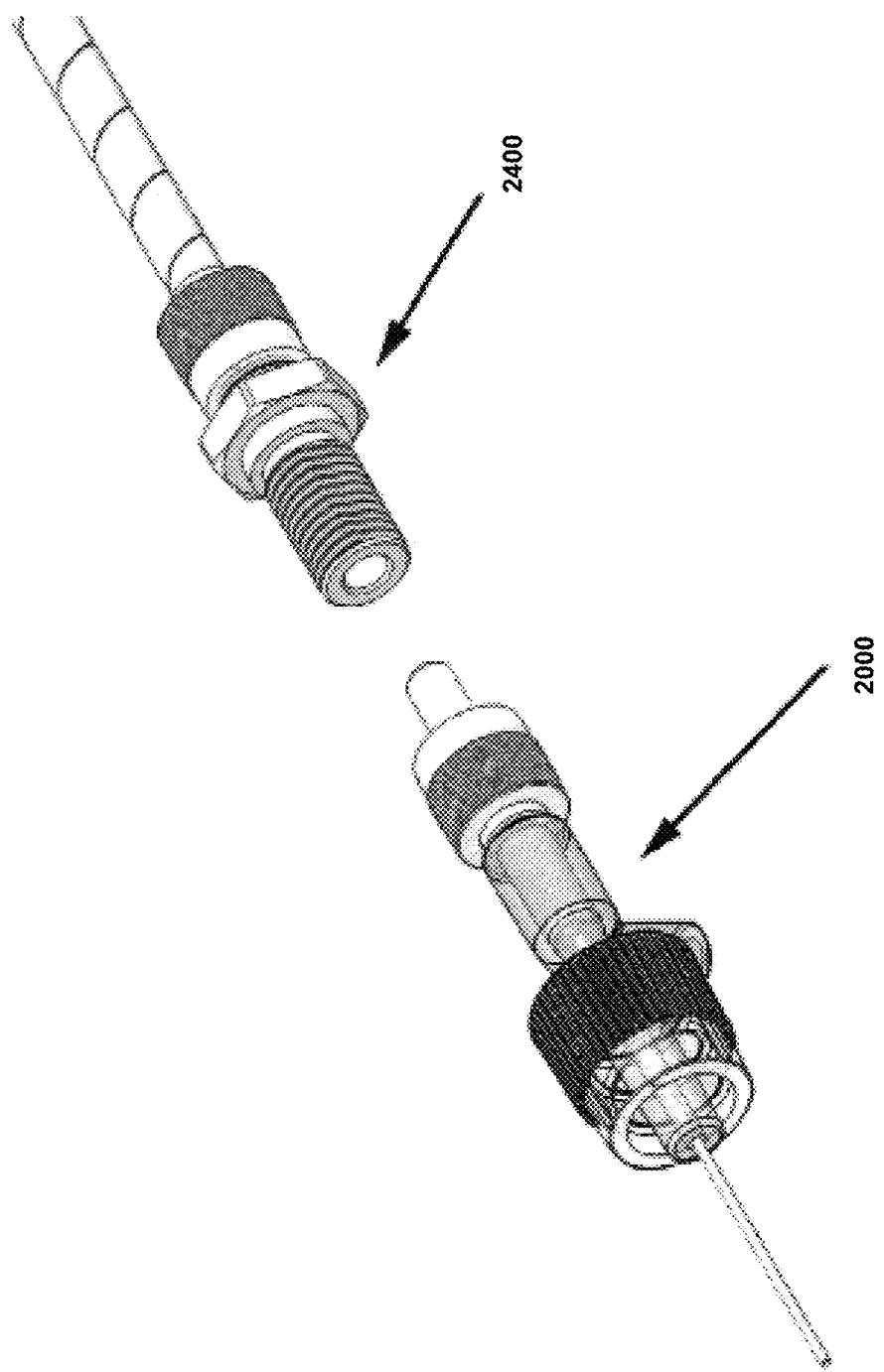
FIG. 26 shows the dry light adapter of FIG. 20 aligned for coupling with the patient cable of FIG. 24.
Figure 27:
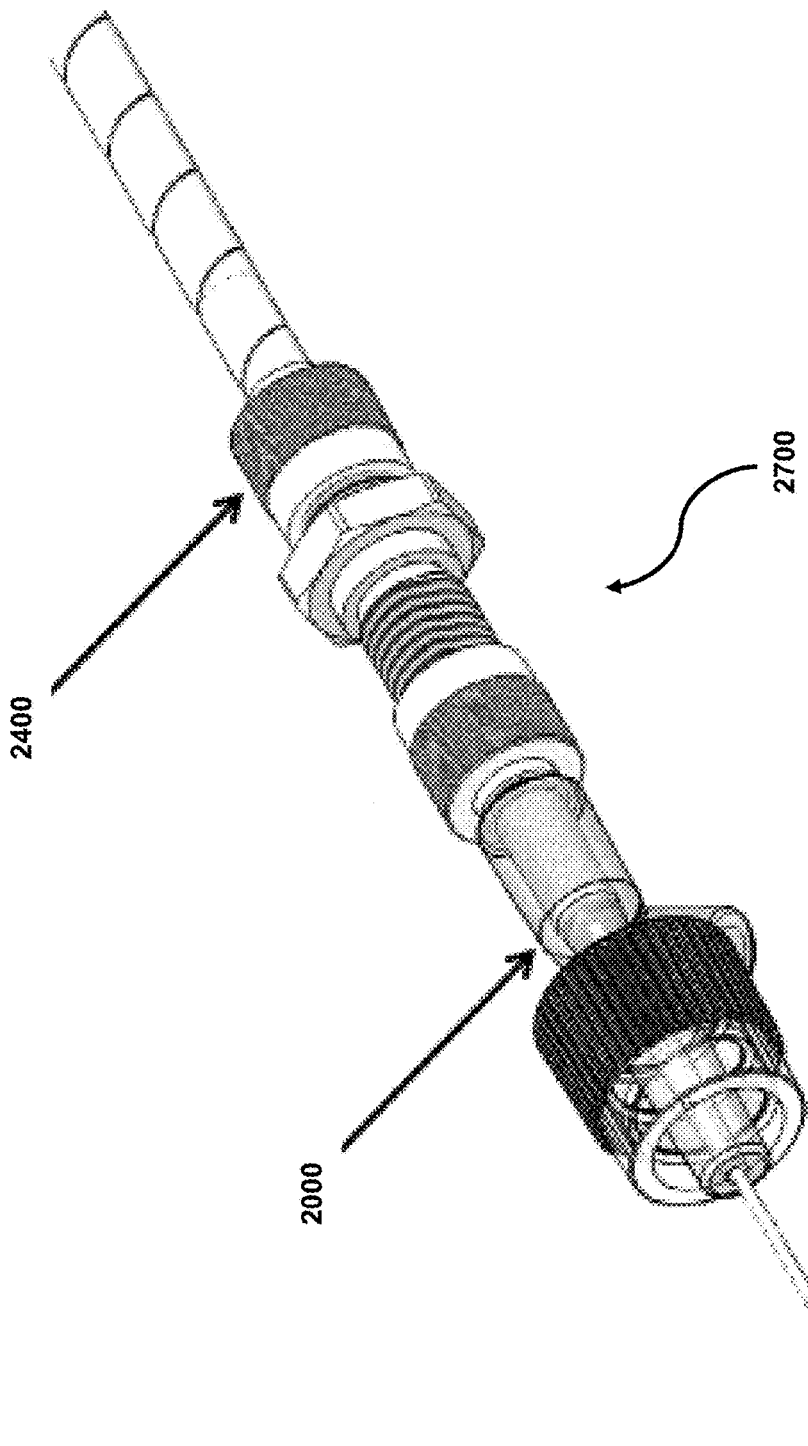
FIG. 27 is an illustration of the coupled dry light adapter and patient cable.

FIG. 26 depicts how a dry light adapter 2000 can be aligned for assembly with a patient cable 2400 in some embodiments of the inventive concept. Such an embodiment permits mating of a standard optical connector incorporated into dry light adapter 2000 with a standard optical connector that forms part of the terminus of a fiber optic cable from a light source via an off the shelf bulkhead connector, without the need for intervening active optics (for example, a lens). This provides an inexpensive, reliable, and efficient connection that is not subject to light loss due to diffraction and scatter. The ferrules of such optical connectors can provide optical losses of 2 dB of attenuation or less if an overmold is present. In addition, the optical interface is isolated from fluids that may be involved in a treatment process. FIG. 27 depicts an assembled exemplary dry light adapter 2000 and exemplary patient cable 2400, collectively referred to as assembly 2700.

Figure 28:
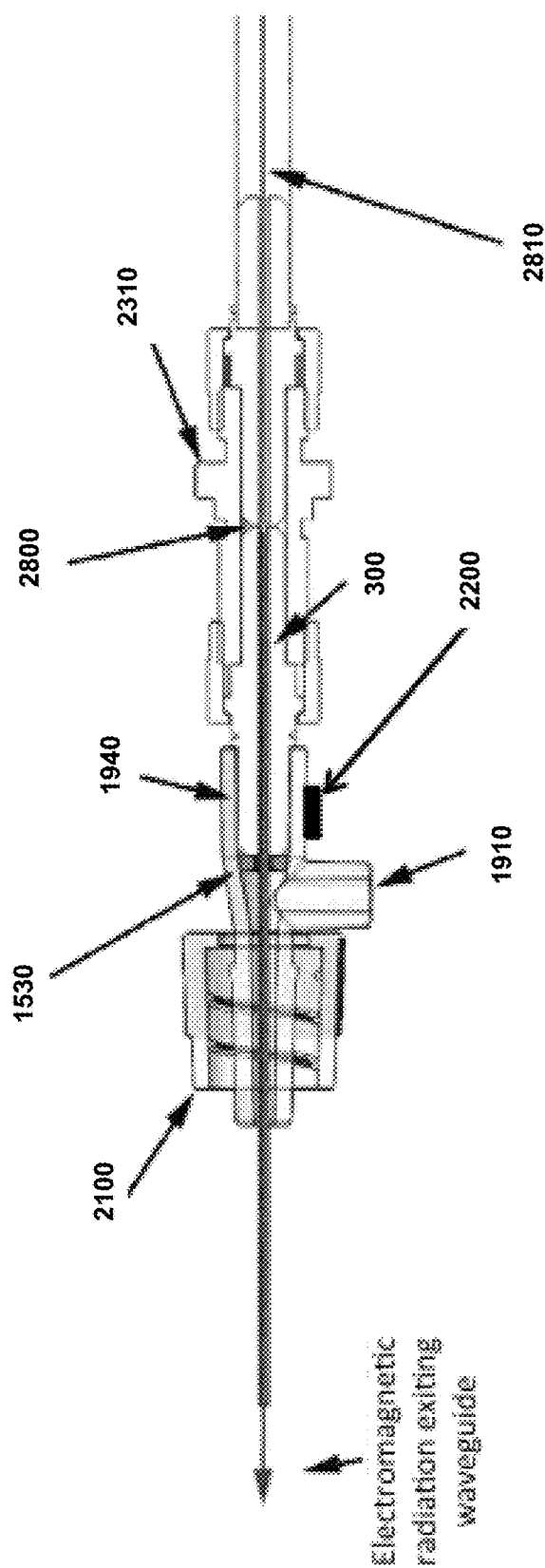
FIG. 28 is a cross-section view of the assembly of FIG. 27.

Alignment of components and flow of electromagnetic energy through assembly 2700 is depicted in FIG. 28, which shows a cross-section view of such an assembly 2700.

Electromagnetic radiation (for example, UV and/or visible light) is supplied by the source optic cable 2810 (within optical cable 2300) and exits from the waveguide 300. The optical interface 2800 between the waveguide 300 and the optical fiber(s) 2810 of the source fiber optic 2300 is within the bulkhead adapter 2310, which provides precise alignment. Use of an O-ring 1530 that seats tightly against an interior surface of the adapter device 1900 and an exterior surface of a SMA connector 1800 associated with the dry light adapter 2000 prevents fluids from reaching the optical interface 2800, preventing contamination of patient cable 2400 and keeping optical performance consistent during use.

Figure 29:
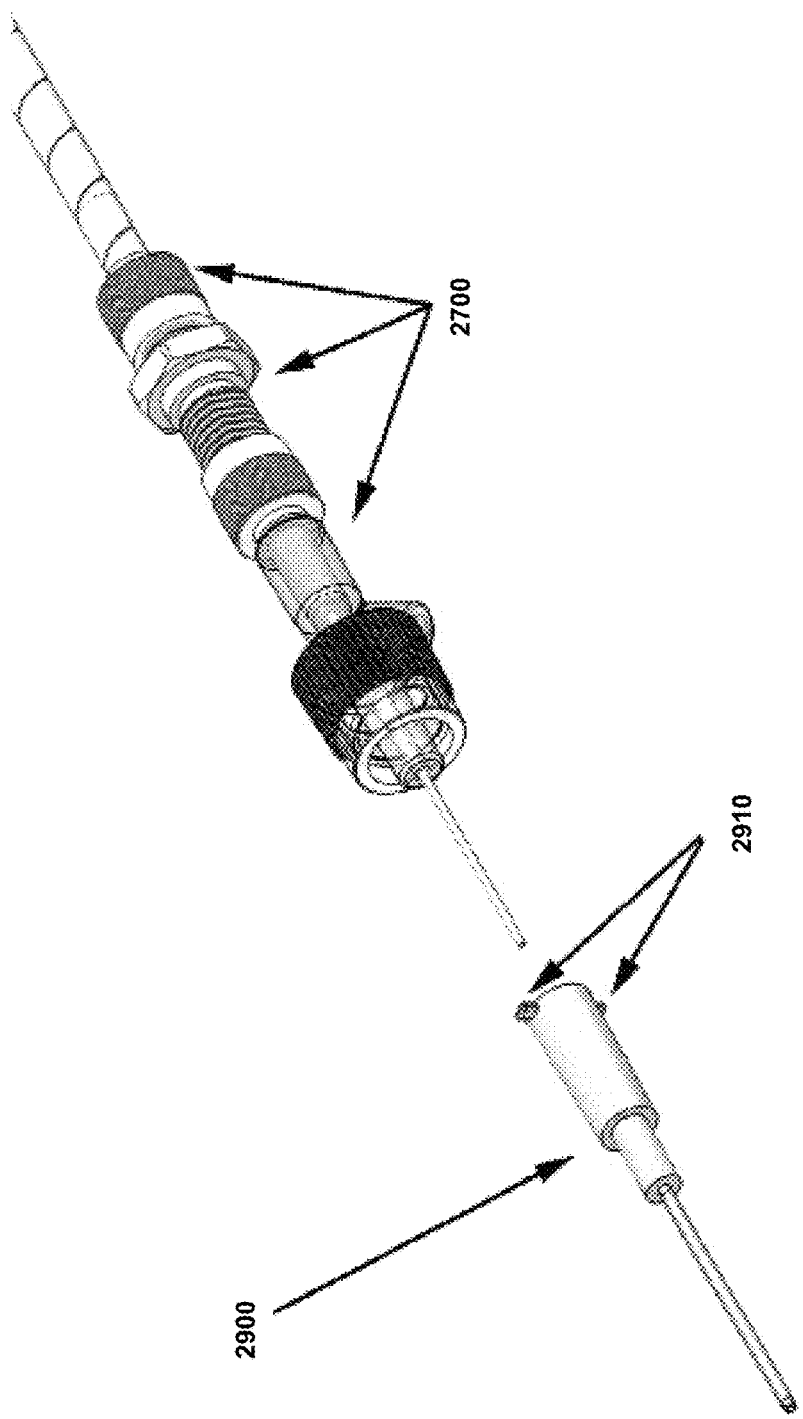
FIG. 29 shows a catheter/cannula aligned for coupling with the assembly of FIG. 27.

As noted above, dry light adapter 2000 can incorporate features that permit attachment of a variety of Luer lock compatible devices for access to venous and/or lymphatic spaces. As shown in FIG. 29, a catheter or cannula 2900 with wings 2910 (such as those described above associated with FIGS. 10-11) suitable for interfacing with a Luer lock ring can be aligned for attachment.

Figure 30:
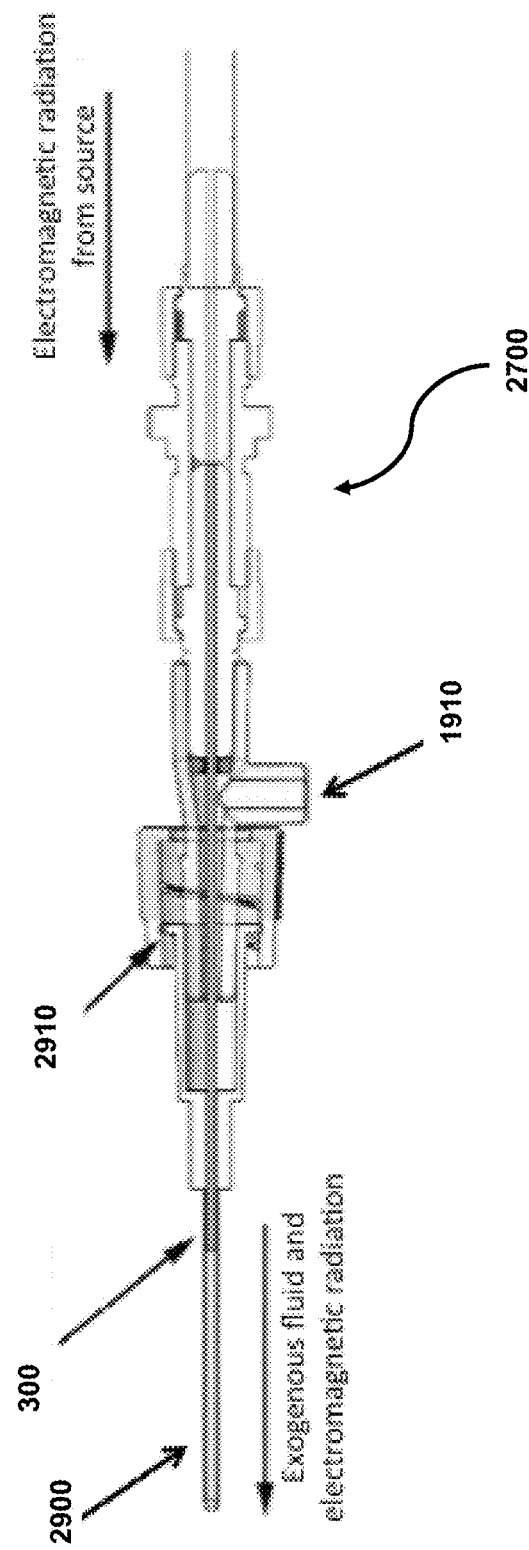
FIG. 30 is a cross-section view of the radiation and fluid flows through the coupled catheter/cannula coupled and dry light adapter/patient cable assembly.
Figure 31:
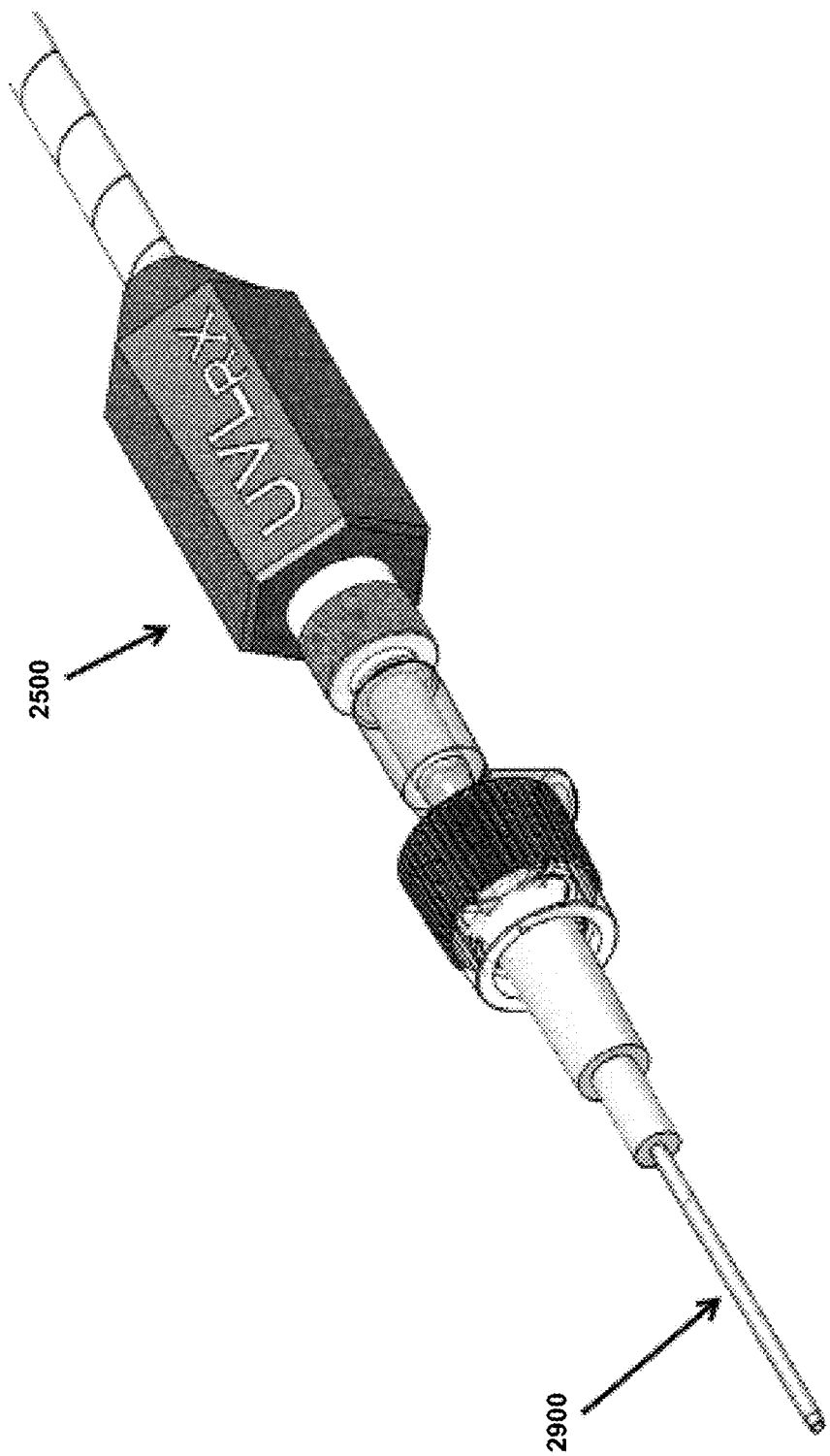
FIG. 31 is an isometric view of the assembly of FIG. 30, with the overmold illustrated in FIG. 25.

FIG. 30 shows a cross section of assembly 2700 with an attached catheter or cannula 2900 that permits access of the waveguide 300 to a venous and/or lymphatic space. Electromagnetic energy from the source is transmitted through the waveguide 300, which can extend partially into the catheter/cannula 2900, and can then exit the waveguide 300 and enter a venous or lymphatic space of an individual undergoing treatment. Exogenous fluid (such as saline) can be supplied through the exogenous fluid inlet 1910, where it can exit through the catheter/cannula 2900 and keep the device free of clots and debris. As noted above, such exogenous fluids may also be selected for therapeutic effect. Similarly, FIG. 31 shows an embodiment of the inventive concept that includes assembly 2900 with an overmold 2500. Such an overmold may be used to house an energizer or reader for machine readable indicia (for example, an RFID tag) that is incorporated into disposable or single-use portions of the device.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for irradiation of a vascular space and its contents, comprising:
    a central section having a first end and second end, the central section comprising:
    a central lumen extending from the first end to the second end;
    an engaging protrusion at the second end; and
    a fluid port configured to introduce an exogenous fluid into the central lumen;
    a vascular access portion extending from the first end of the central section, comprising an access lumen in fluid communication with the central lumen;
    a tapered terminus extending from the second end of the central section, the tapered end including:
    at least two contiguous, intersecting channels arranged in a linear series and radially rotated from each other; and
    a segmented waveguide lumen formed from an intersection of the at least two contiguous, intersecting channels, wherein the segmented waveguide lumen is aligned with the central lumen and the access lumen and wherein the segmented waveguide lumen is fluidly isolated from the central lumen; and
    a waveguide housed within the segmented waveguide lumen, wherein the waveguide includes a first end approximately flush with the tapered end and extends through the central lumen and the access lumen.

2. The device of claim 1, wherein the waveguide comprises an optical fiber.

3. The device of claim 1, wherein the device is configured to connect with a catheter.

4. The device of claim 3, wherein the waveguide extends at least partially into the catheter.

5. The device of claim 1, wherein the device further comprises machine readable indicia.

6. The device of claim 5, wherein the machine readable indicia includes at least one of a unique identifier of an adapter device, a part number of the adapter device, a lot number of the adapter device, and an expiration date of the adapter device.

* * * * *